US011793448B2

(12) United States Patent
Shimizu

(10) Patent No.: US 11,793,448 B2
(45) Date of Patent: Oct. 24, 2023

(54) DETECTION DEVICE

(71) Applicant: CITIZEN WATCH CO., LTD., Tokyo (JP)

(72) Inventor: Hideki Shimizu, Saitama (JP)

(73) Assignee: CITIZEN WATCH CO., LTD., Tokyo (JP)

(*) Notice: Subject to any disclaimer, the term of this patent is extended or adjusted under 35 U.S.C. 154(b) by 1025 days.

(21) Appl. No.: 16/343,420

(22) PCT Filed: Oct. 13, 2017

(86) PCT No.: PCT/JP2017/037237
§ 371 (c)(1),
(2) Date: Apr. 19, 2019

(87) PCT Pub. No.: WO2018/074371
PCT Pub. Date: Apr. 26, 2018

(65) Prior Publication Data
US 2019/0269361 A1  Sep. 5, 2019

(30) Foreign Application Priority Data
Oct. 21, 2016 (JP) ................... 2016-207030

(51) Int. Cl.
*A61B 10/00* (2006.01)
*A61B 5/00* (2006.01)
(Continued)

(52) U.S. Cl.
CPC .......... *A61B 5/4088* (2013.01); *A61B 5/0077* (2013.01); *A61B 5/02405* (2013.01);
(Continued)

(58) Field of Classification Search
CPC . A61B 5/4088; A61B 5/0077; A61B 5/02405; A61B 5/02416; A61B 5/02438;
(Continued)

(56) References Cited

U.S. PATENT DOCUMENTS 7,453,539 B2 * 11/2008 Matsuoka ......... G02F 1/134363
349/39
9,737,255 B2 *  8/2017 Chen .................... A61B 5/7475
(Continued)

FOREIGN PATENT DOCUMENTS

CN     1870939 A   11/2006
CN   105263403 A    1/2016
(Continued)

OTHER PUBLICATIONS

WIPO, International Search Report for PCT/JP2017/037237, dated Dec. 12, 2017.
(Continued)

*Primary Examiner* — Hai Phan
*Assistant Examiner* — Anthony D Afrifa-Kyei

(57) ABSTRACT

A detection device detecting changes in positive and negative feelings related to mild cognitive impairment is provided. This detection device includes: a detector detecting heartbeat information of a subject; a calculating unit calculating a maximum Lyapunov exponent from the heartbeat information, the maximum Lyapunov exponent indicating to what extent heartbeat intervals vary; a feeling determination unit determining whether the subject has a negative feeling with brain fatigue, anxiety or depression, or a positive feeling without brain fatigue, anxiety and depression, based on the maximum Lyapunov exponent; a change determination unit determining whether the positive or negative feeling of the subject has changed, based on frequency of occurrence of the negative or positive feeling in a predetermined period; and an output unit outputting a result of determination by the change determination unit.

21 Claims, 16 Drawing Sheets

(51) Int. Cl.
*A61B 5/024* (2006.01)
*A61B 5/1171* (2016.01)
*A61B 5/16* (2006.01)
*G06V 40/16* (2022.01)

(52) U.S. Cl.
CPC ...... *A61B 5/02416* (2013.01); *A61B 5/02438* (2013.01); *A61B 5/1176* (2013.01); *A61B 5/165* (2013.01); *A61B 5/486* (2013.01); *A61B 5/6898* (2013.01); *A61B 5/742* (2013.01); *A61B 5/7405* (2013.01); *A61B 5/7475* (2013.01); *A61B 10/00* (2013.01); *G06V 40/161* (2022.01); *A61B 5/4848* (2013.01); *A61B 2503/08* (2013.01); *A61B 2505/07* (2013.01)

(58) Field of Classification Search
CPC ....... A61B 5/1176; A61B 5/165; A61B 5/486; A61B 5/6898; A61B 5/7405; A61B 5/742; A61B 5/7475; A61B 10/00; A61B 5/4848; A61B 2503/08; A61B 2505/07; A61B 5/0245; A61B 5/18; A61B 5/00; A61B 5/16; A61B 5/4035; A61B 5/7239; A61B 5/024; G06V 40/161; G16H 40/63; G16H 50/50; G16H 50/20; A61M 21/02; A61M 15/02; A61M 2021/0027; A61M 2021/0044; A61M 2021/005; A61M 21/00; A61M 2021/0005

See application file for complete search history.

(56) References Cited

U.S. PATENT DOCUMENTS

| | | | |
|---|---|---|---|
| 10,357,210 B2* | 7/2019 | Zizi | A61B 5/117 |
| 2004/0107105 A1 | 6/2004 | Shomi et al. | |
| 2005/0131273 A1 | 6/2005 | Asano et al. | |
| 2007/0068970 A1* | 3/2007 | Hanaoka | B65G 33/22 |
| | | | 222/240 |
| 2007/0078351 A1 | 4/2007 | Fujita et al. | |
| 2010/0179441 A1* | 7/2010 | Kanai | A61B 5/02116 |
| | | | 600/300 |
| 2012/0016255 A1 | 1/2012 | Masuo | |
| 2013/0066395 A1* | 3/2013 | Simon | A61N 1/36003 |
| | | | 607/48 |
| 2013/0144111 A1 | 6/2013 | Wang et al. | |
| 2016/0081630 A1 | 3/2016 | Aoshima | |
| 2016/0296123 A1* | 10/2016 | Plans Casal | A61B 5/0205 |
| 2016/0328533 A1 | 11/2016 | Kawai et al. | |
| 2017/0278073 A1* | 9/2017 | Anjo | G06Q 10/1097 |

FOREIGN PATENT DOCUMENTS

| | | |
|---|---|---|
| CN | 105595961 A | 5/2016 |
| JP | H07-231880 A | 9/1995 |
| JP | H9-322943 | 12/1997 |
| JP | 2002-143097 A | 5/2002 |
| JP | 2002-306492 A | 10/2002 |
| JP | 2004-222818 A | 8/2004 |
| JP | 2005-137896 A | 6/2005 |
| JP | 2007-50144 A | 3/2007 |
| JP | 2008-532587 A | 8/2008 |
| JP | 2011-161137 A | 8/2011 |
| JP | 2012-035057 A | 2/2012 |
| JP | 2012-045162 A | 3/2012 |
| JP | 2013-027570 A | 2/2013 |
| JP | 2015016273 A * | 1/2015 |
| JP | 2006-204502 A | 8/2016 |
| JP | 2017-063963 A | 4/2017 |
| JP | 2017-063966 A | 4/2017 |
| JP | 2009-022610 A | 2/2019 |
| WO | 2006/090371 A2 | 8/2006 |
| WO | WO2014/002276 A1 | 1/2014 |
| WO | WO2015/107710 A1 | 7/2015 |

OTHER PUBLICATIONS

WIPO, Written Opinion for PCT/JP2017/037237, dated Dec. 12, 2017.
Japan Patent Office, Office Action for Japanese Patent Application No. 2019-057291, dated May 12, 2020 (a machine translation thereof is attached hereto).
Japan Patent Office, Office Action for Japanese Application No. 2020-110639, dated Jun. 1, 2021.
Japan Patent Office, Office Action for Japanese Patent Application No. 2022-045788, dated Feb. 7, 2023.
Chinese National Intellectual Property Administration, Office Action including Search Report for Chinese Patent Application No. 201780064945.1, dated Jan. 6, 2022.

* cited by examiner

FIG. 2
(A)
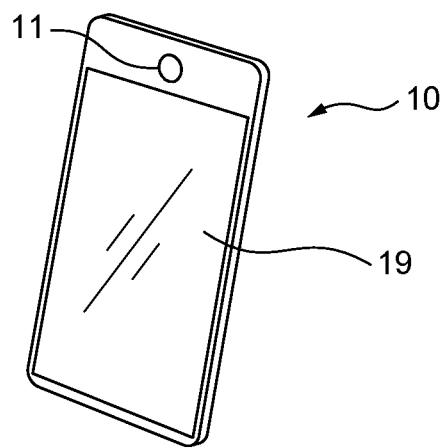
(B)
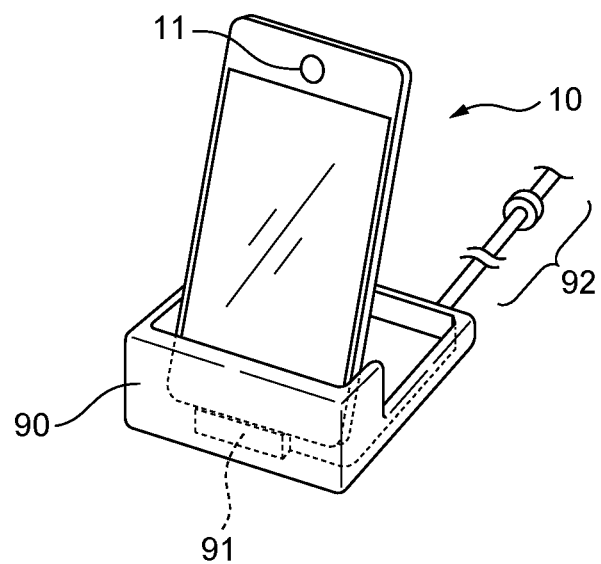

FIG. 4
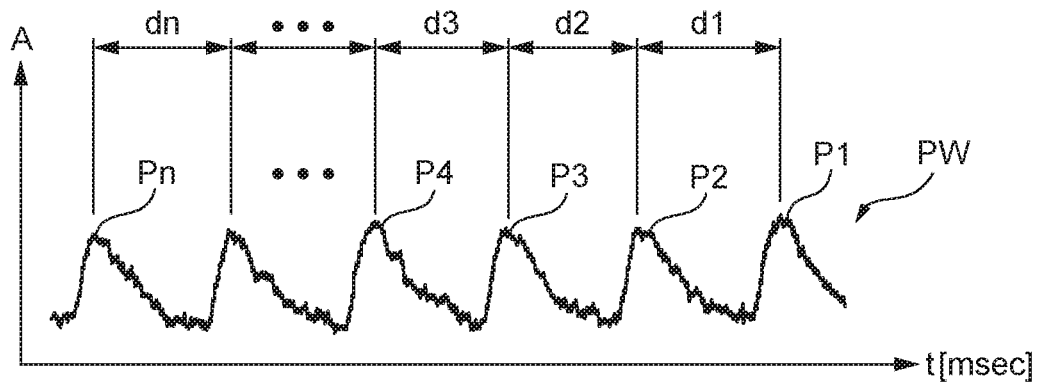
(A)
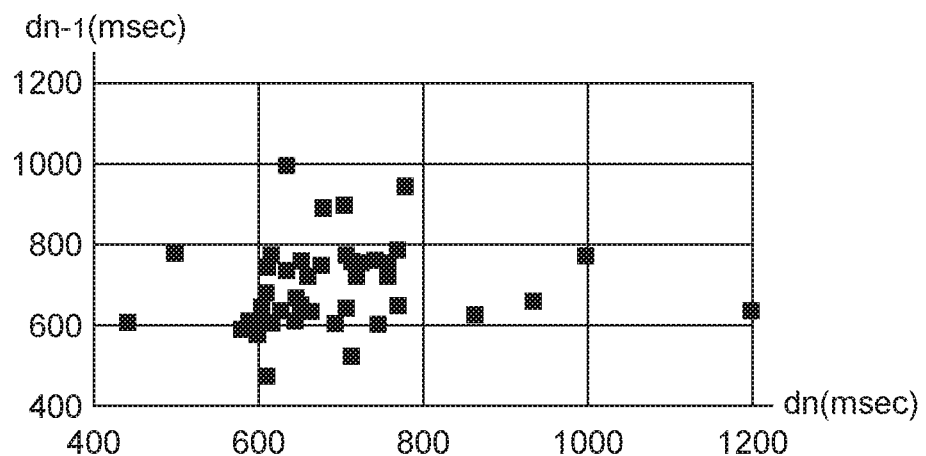
(B)
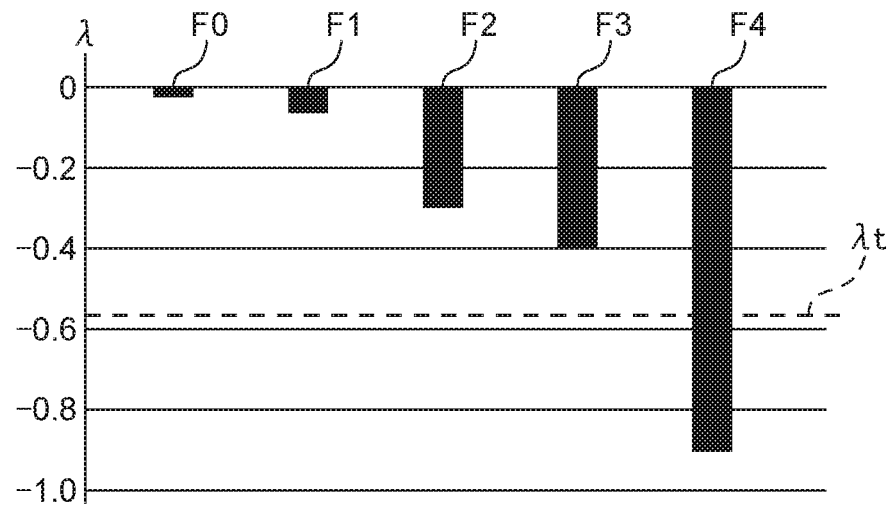
(C)

FIG. 13
(A)
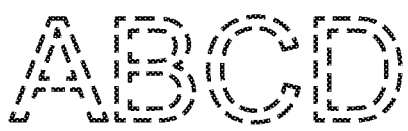
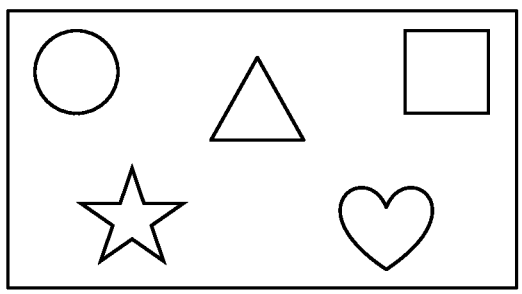
(D)
(B)
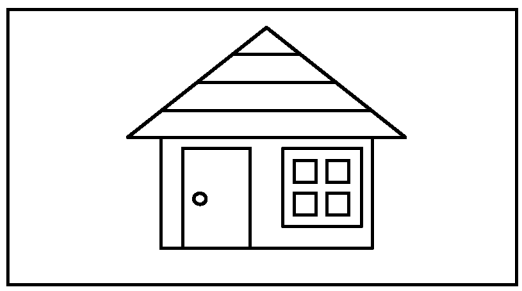
(E)
(C)
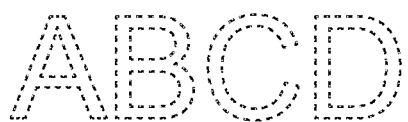
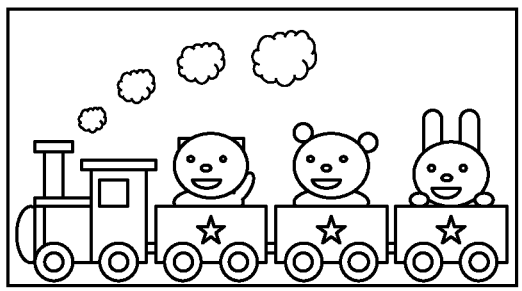
(F)

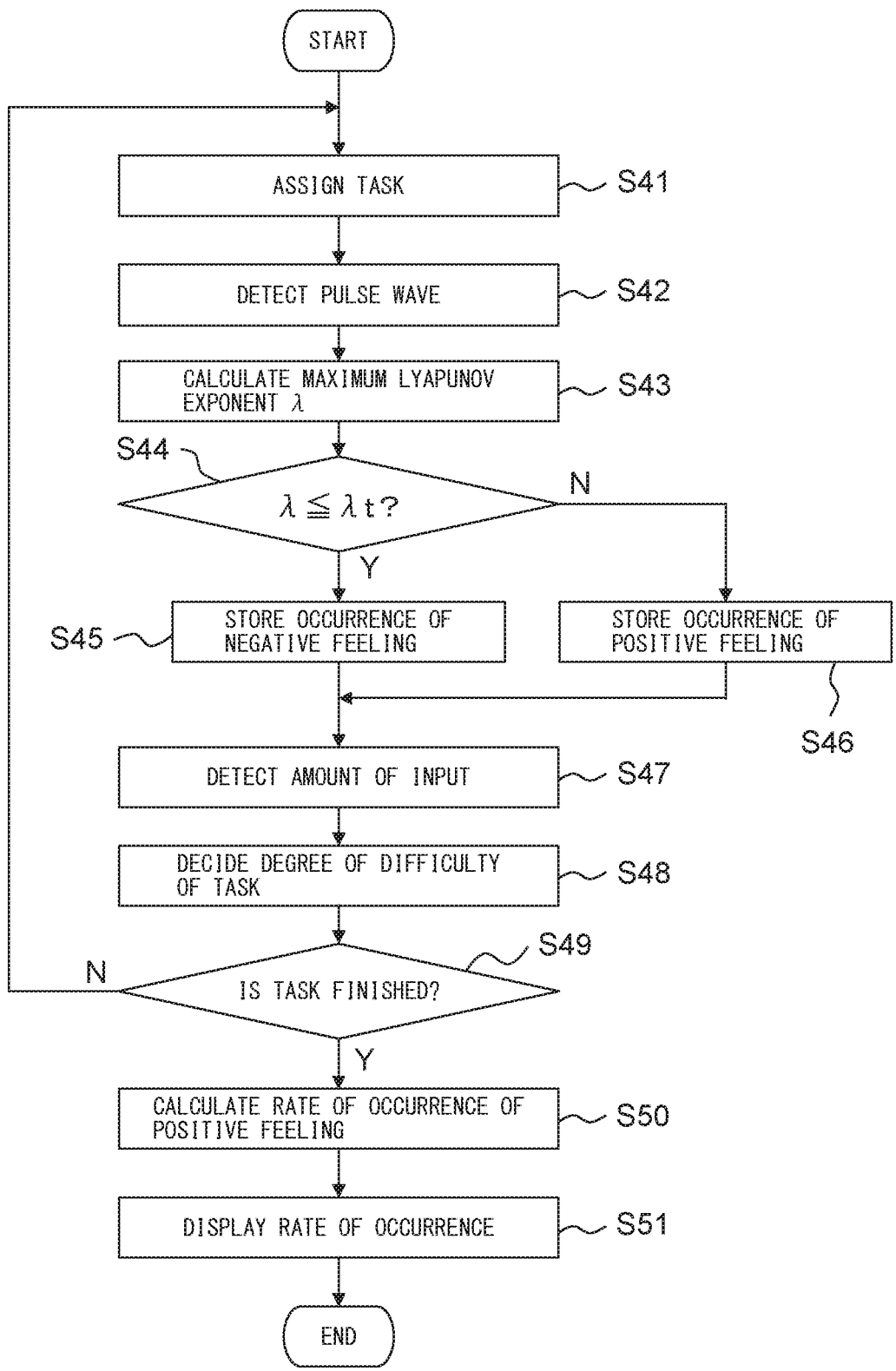

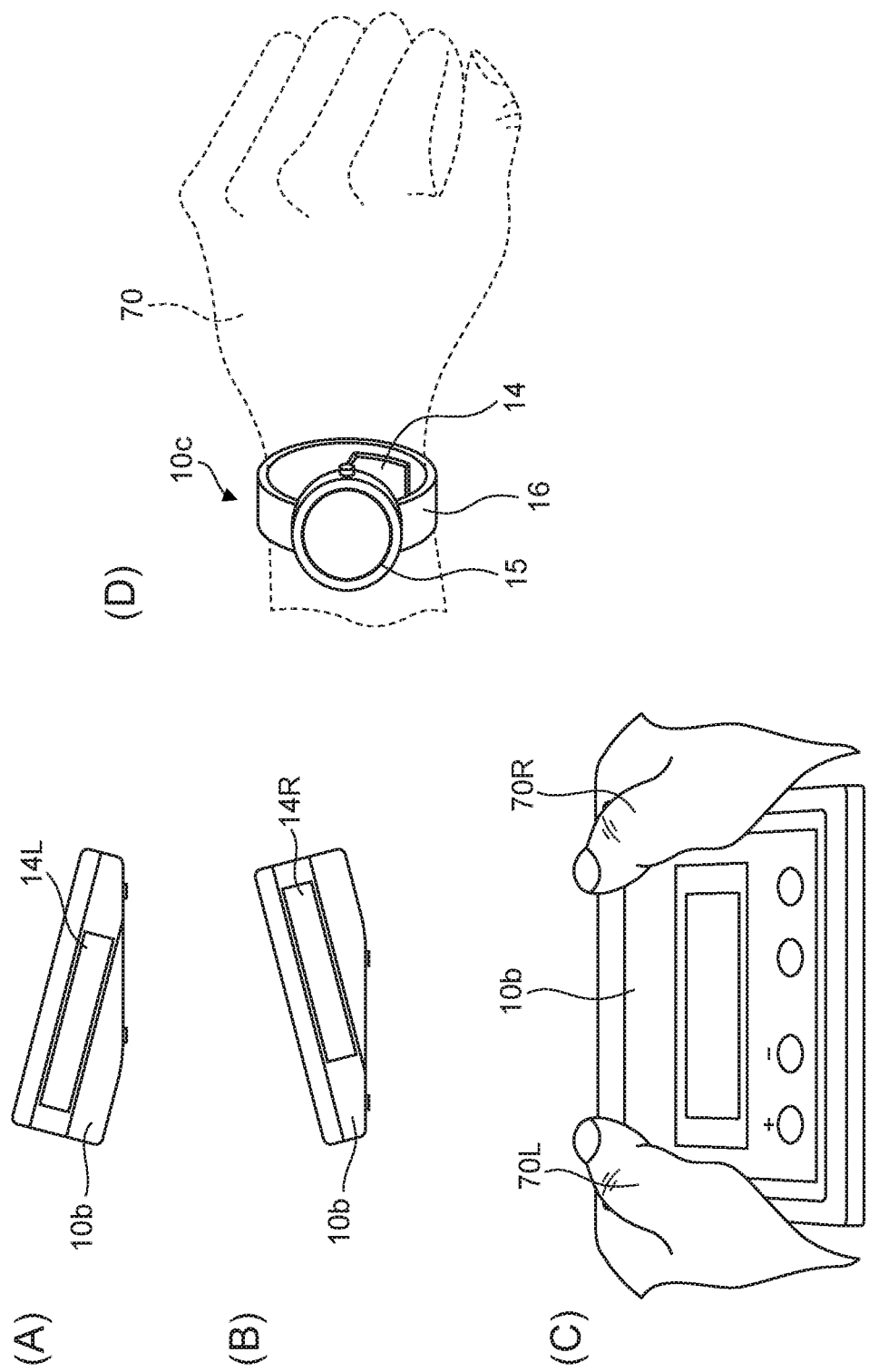

DETECTION DEVICE

FIELD

The present invention relates to a detection device detecting changes in positive and negative feelings related to mild cognitive impairment (hereinafter referred to as "MCI"), which is an early symptom of senile dementia.

BACKGROUND

Patent Literature 1 describes a system and method for predicting and notifying appearance of a disease. This system measures user's vital phenomena to obtain their data, and, while continuously monitoring it, compares the data with user-specific score data previously stored in a scoring table for determination to decide a level for predicting appearance of a disease, and notifies the level to the user.

Patent Literature 2 describes an apparatus for measuring degrees of mental immunity. This apparatus includes a unit for measuring biological information, a means for forming an attractor from the biological information, a means for calculating a Lyapunov exponent and its characteristic value based on the attractor, and a means for judging the degree of mental immunity, such as an ability to communicate or the degree of dementia, based on the characteristic value.

Patent Literature 3 describes an apparatus and program for diagnosing a psychiatric disorder. This apparatus includes a means for measuring an electrocardiogram of a person to be diagnosed, a means for causing a load test on the person to be conducted, a means for calculating a coefficient of variations in R-R intervals of the electrocardiogram based on measured electrocardiographic data, a means for determining that there is a possibility of a psychiatric disorder if the calculated coefficient after the load test is smaller than the coefficient before the load test, and a means for displaying the result of determination.

Patent Literatures 4, 5 describe a fatigue degree meter which senses a subject's biological signal related to a circulatory organ, calculates the degree of variations in heartbeat intervals of the subject from the sensed biological signal, refers to a correspondence between degrees of variations in heartbeat intervals and degrees of brain fatigue, based on the calculated value, to obtain the degree of brain fatigue of the subject, and outputs information on the degree of fatigue.

CITATION LIST

Patent Literature

Patent Literature 1: Japanese Unexamined Patent Publication No. 2002-143097
Patent Literature 2: Japanese Unexamined Patent Publication No. 2006-204502
Patent Literature 3: Japanese Unexamined Patent Publication No. 2012-045162
Patent Literature 4: Japanese Unexamined Patent Publication No. 2017-063963
Patent Literature 5: Japanese Unexamined Patent Publication No. 2017-063966

SUMMARY

Senile dementia is an incurable disease, and is deemed a grave psychiatric disorder since its progression leads to difficulties in living an ordinary life in society for such a reason as lack of the ability to communicate. Appearance of senile dementia can be prevented or delayed by medicines if it is successfully detected at the stage of MCI, which is an early symptom before appearance of the disease. However, technologies to achieve determination or detection of MCI have not yet been disclosed. The technologies disclosed in Patent Literatures 1 to 3 merely detect a symptom of dementia or degrees of mental immunity to disease appearance.

MCI sufferers frequently forget things and feel depressed. It is generally difficult to distinguish such forgetfulness from what is caused by senility, and to distinguish such a depressed feeling from pseudodementia caused by senile depression. However, it is known that MCI and pseudodementia have a difference in patterns of occurrence of a negative feeling, which is a feeling with brain fatigue, anxiety or depression. In order to detect appearance of senile dementia in its early stages and minimize the disease progression and worsening, it is desirable to speedily and surely detect changes in the negative feeling or in the opposite, i.e., a positive feeling.

It is an object of the present invention to provide a detection device detecting changes in positive and negative feelings related to mild cognitive impairment.

Provided is a detection device includes: a detector detecting heartbeat information of a subject; a calculating unit calculating a maximum Lyapunov exponent from the heartbeat information, the maximum Lyapunov exponent indicating to what extent heartbeat intervals vary; a feeling determination unit determining whether the subject has a negative feeling with brain fatigue, anxiety or depression, or a positive feeling without brain fatigue, anxiety and depression, based on the maximum Lyapunov exponent; a change determination unit determining whether the positive or negative feeling of the subject has changed, based on frequency of occurrence of the negative or positive feeling in a predetermined period; and an output unit outputting a result of determination by the change determination unit.

Preferably, the predetermined period is three months or longer, and the change determination unit determines whether the subject suffers from mild cognitive impairment, based on the period and times of occurrence of the negative feeling as the frequency of occurrence. Preferably, the change determination unit determines whether the subject suffers from mild cognitive impairment, based on intra-day variations in the number of occurrences of the negative feeling.

Preferably, the detector continuously captures images of a facial region of the subject automatically without any operations by the subject at least twice a day, morning and afternoon, during the predetermined period, and detects the heartbeat information based on variations in luminance of the captured images. Preferably, the feeling determination unit determines the feeling of the subject based on the heartbeat information detected from the continuously captured images if the amount of movement of the facial region in the images falls within a predetermined range.

Preferably, the detection device further includes a feeling controller conducting guidance so that the subject concentrates and is lead to the positive feeling, wherein the predetermined period is a period during which the feeling controller continues the guidance, and the output unit is a display which shows a result of determination by the feeling determination unit during the guidance and a result of determination by the change determination unit after the guidance.

Preferably, the feeling controller prompts the subject to draw a deep breath such that exhalation is slower than inhalation, thereby causing the subject to concentrate on breathing. Preferably, the feeling controller notifies the subject of timings of the inhalation and exhalation with a screen of the display.

Preferably, the feeling controller plays music including a phrase longer than the period of breathing, thereby causing the subject to concentrate on the music. Preferably, the feeling controller controls the tempo of the music according to the heart rate of the subject calculated from the heartbeat information.

Preferably, the output unit is a display, the detection device further includes: an input unit; and an assigning unit assigning a task which requires input of the subject for processing an object shown on the display, wherein the predetermined period is a period during which the assigning unit assigns the task, and the display shows the task and shows a result of determination by the change determination unit after the task is finished.

Preferably, the detection device further includes: a memory storing tasks assigned by the assigning unit, the tasks varying in degree of difficulty; and an input detector detecting the amount of input for processing the object, wherein the assigning unit repeatedly assigns tasks with different degrees of difficulty, according to the frequency of occurrence of the negative or positive feeling and the amount of input in the predetermined period.

Preferably, the assigning unit assigns, as the task, one which requires coloring in regions divided by lines shown on the display, or one which requires copying letters shown on the display onto the display by hand. Preferably, the display shows to what extent the negative feeling has changed to the positive feeling, based on frequency of occurrence of the positive feeling in the predetermined period, as the result of determination by the change determination unit.

The detection device can detect changes in positive and negative feelings related to MCI.

BRIEF DESCRIPTION OF DRAWINGS

FIGS. 2(A) and 2(B) are perspective views showing the outward appearance of the image capturing unit 10.

FIGS. 4(A) to 4(C) are graphs for explaining how to determine the presence of the negative feeling based on a pulse wave.

FIGS. 13(A) to 13(F) are diagrams showing examples of tasks assigned by the prevention device 3.

FIG. 15 is a flowchart showing an operational example of the prevention device 3.

FIGS. 16(A) to 16(D) are diagrams showing detectors 10b, 10c.

DESCRIPTION OF EMBODIMENTS

Figure 1:
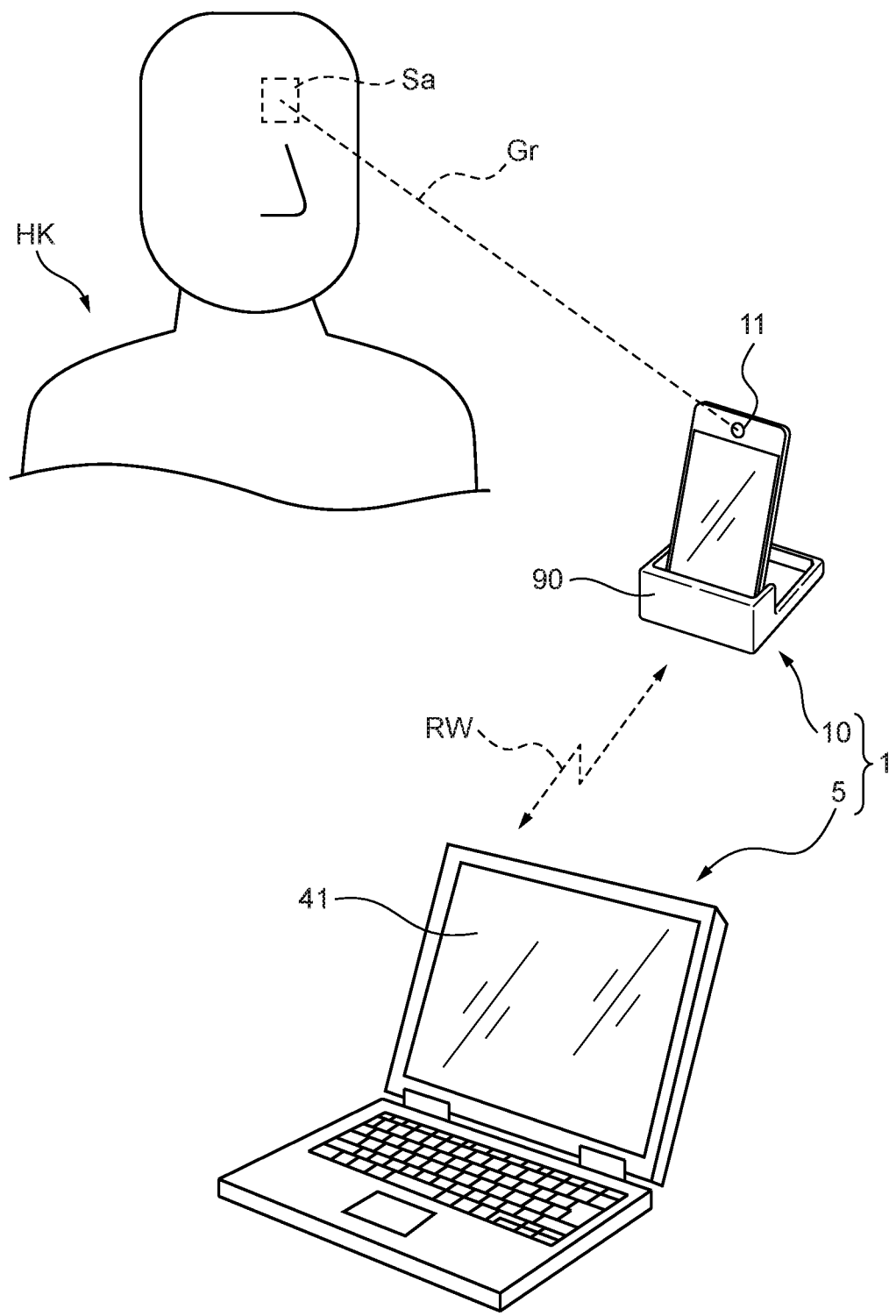
FIG. 1 is a perspective view showing a detection device 1 in use.

Hereinafter, with reference to the accompanying drawings, exemplary embodiments will be explained in detail. In the drawings, the same components will be assigned the same reference numeral. The drawings may be exaggerated for illustrative purposes. Since the following embodiments and drawings describe merely examples, the invention may be otherwise practiced without departing from its spirit or scope.

FIG. 1 is a perspective view showing a detection device 1 in use.

As shown in FIG. 1, the detection device 1 includes an image capturing unit 10 and an information terminal 5. In the illustrated example, the image capturing unit 10 is a portable device, such as a smartphone, while the information terminal 5 is a notebook PC. However, the invention is not limited thereto. The image capturing unit 10 may be a tablet device or digital camera, and the information terminal 5 may be a tablet device or specifically-designed processor. Alternatively, the image capturing unit 10 and information terminal 5 may be integrated into a single device.

The detection device 1 is not a device measuring the level of senile dementia after appearance of the disease, but a device detecting appearance of MCI, which is an early symptom before appearance of senile dementia. Sufferers of MCI or pseudodementia also exhibit brain fatigue, anxiety or depression (hereinafter referred to as "negative feeling") and forgetfulness. However, the following facts are known: since pseudodementia is a disorder caused by malfunction of autonomic nerves, it often leads to intra-day variations in the number of occurrences of the negative feeling, and causes a symptom continuing for weeks or months; in contrast, MCI does not lead to intra-day variations in the number of occurrences of the negative feeling, but causes a negative feeling continuing for several days or several months.

As disclosed in Patent Literatures 4, 5, for example, a technique is known to calculate a maximum Lyapunov exponent indicating the degree of variations in heartbeat intervals from time-series data of heartbeat intervals or pulse intervals, and quantify the degree of brain fatigue, anxiety or depression based on the calculated value. Actually, a pulse (sphygmus) is more easily measured than a heartbeat, and using pulse intervals instead of heartbeat intervals causes no problem as long as the tendency for changes in feelings is examined. Thus, the detection device 1 measures the pulse wave of a subject, for example, at least twice a day, morning and afternoon, calculates a maximum Lyapunov exponent indicating the degree of variations in pulse intervals, and determines whether the subject has a negative feeling, based on the calculated value. The detection device 1 then determines whether the negative feeling continues for several months, based on frequency of occurrence of the negative feeling (patterns of occurrence thereof) by the month, and notifies the outside if it detects a sign specific to MCI.

FIGS. 2(A) and 2(B) are perspective views showing the outward appearance of the image capturing unit 10. FIG. 2(B) shows the image capturing unit 10 set on a stand 90 for holding it. As shown in FIG. 2(A), the image capturing unit 10 includes an image sensor 11 and a touch-screen display 19 for customizing operations of the image capturing unit 10. As shown in FIG. 2(B), the stand 90 includes a built-in connector 91 for battery charging and a power cable 92, which is connected to commercial power to charge the image capturing unit 10.

In particular, some elderly people are frightened of measurement, unwilling to conduct a measurement, including wearing a sensor for measurement, or temporarily have a negative feeling only by hearing an explanation of measurement; therefore, the negative feeling may not be correctly measured in some cases. Thus, the detection device 1 uses the image capturing unit 10 including an image sensor (camera) 11 to capture images of an exposed portion of subject's skin (for example, a facial region, such as a forehead or cheek) so that the measurement may not cause stress. The detection device 1 then extracts variations in luminance synchronized with the blood flow from the captured images, thereby automatically detecting a pulse-wave signal, which is heartbeat information of the subject, without touching the subject and being noticed by him/her.

The image sensor 11 is a CMOS (complementary metal-oxide semiconductor) or CCD (charge-coupled device) image sensor, for example. In each measurement, the image sensor 11 continuously captures images Gr of a measurement frame Sa in the forehead of a subject HK, for example, automatically without any operations by the subject, as shown in FIG. 1. The image capturing unit 10 has the function of automatically tracking the measurement frame Sa by a built-in application program of facial recognition. Thus, even if the subject HK moves around the image capturing unit 10, the pulse wave of the subject HK can be detected. As shown in FIG. 1, the image capturing unit 10 transmits captured image data of the subject HK to the information terminal 5 through radio waves RW by its built-in wireless communication function.

Figure 3:
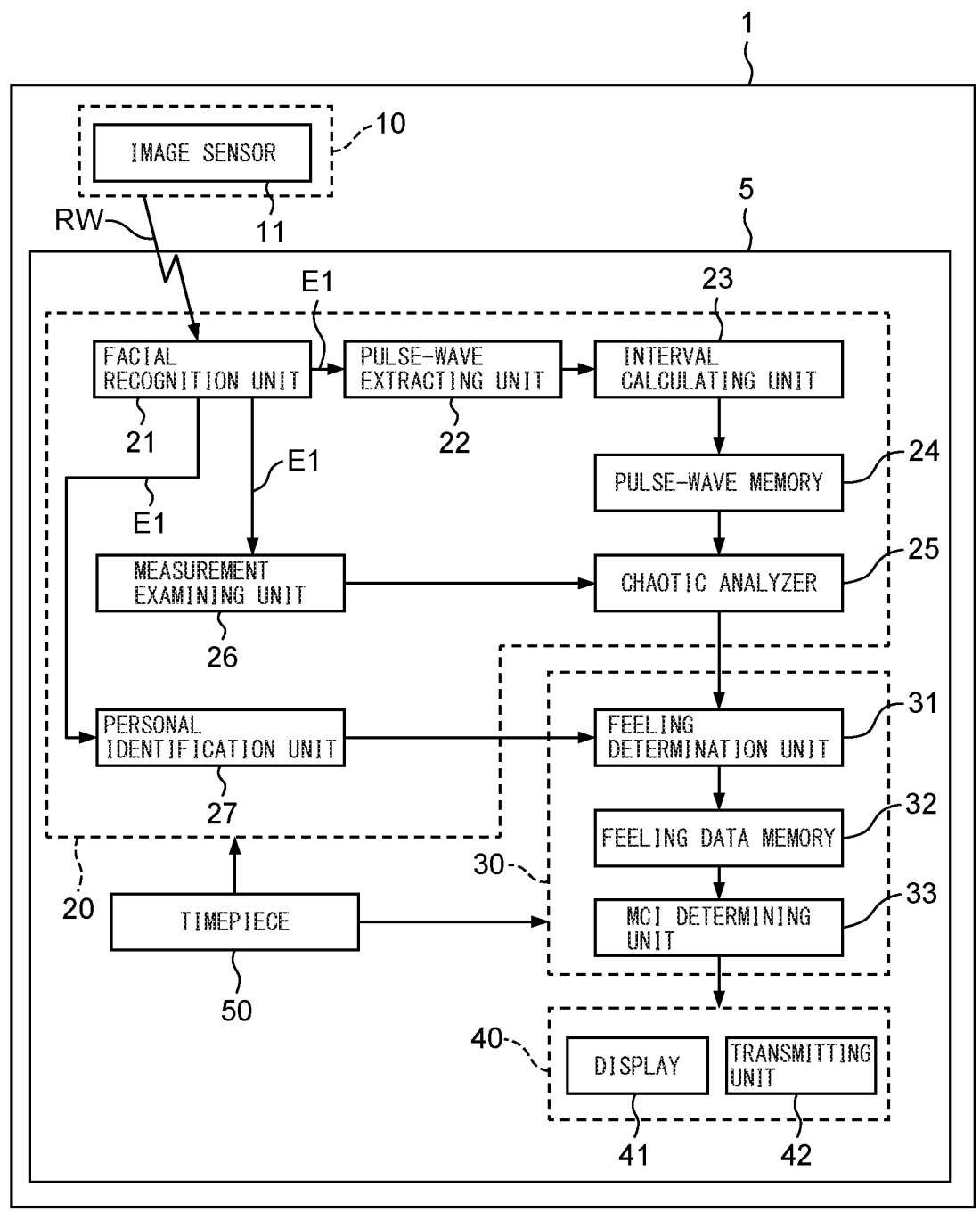
FIG. 3 is a block diagram of the detection device 1.

FIG. 3 is a block diagram of the detection device 1. As shown in FIG. 3, the information terminal 5 of the detection device 1 includes a feeling detector 20, a determining unit 30, a notifying unit 40 and a timepiece 50. The feeling detector 20 includes a facial recognition unit 21, a pulse-wave extracting unit 22, an interval calculating unit 23, a pulse-wave memory 24, a chaotic analyzer 25, a measurement examining unit 26 and a personal identification unit 27. The determining unit 30 includes a feeling determination unit 31, a feeling data memory 32 and an MCI determining unit 33. The notifying unit 40 includes a display 41 and a transmitting unit 42. The pulse-wave memory 24 and feeling data memory 32 are constructed from a hard disk or semiconductor memory. The display 41 is a liquid crystal display, and the timepiece 50 is constructed from a known clock circuit. The other components are realized as software by a microcomputer including a CPU, ROM and RAM in the information terminal 5.

The facial recognition unit 21 applies an edge detection or feature extraction algorithm to the images Gr of the subject HK captured by the image sensor 11, thereby analyzing facial features and selecting an exposed skin portion, such as the forehead, as a measurement region. The facial recognition unit 21 outputs a time-series signal E1, which is data indicating the skin color in the measurement region, to the pulse-wave extracting unit 22, measurement examining unit 26 and personal identification unit 27.

The pulse-wave extracting unit 22 extracts a pulse-wave signal of the subject HK from the time-series signal E1, and outputs the extracted signal to the interval calculating unit 23. Since capillary arteries densely exist inside the measurement frame Sa in the forehead of the subject HK, luminance of the images Gr varies in synchronization with the blood flow of the subject HK. Since variations in intensity of green light of the images Gr reflect the pulse wave (variations in blood flow) most, the pulse-wave extracting unit 22 uses a band-pass filter transmitting frequencies in a range from about 0.5 to 3 Hz including frequencies of human pulse waves, to extract a pulse-wave signal from the component of variations in intensity of green light of the time-series signal E1.

The image capturing unit 10, facial recognition unit 21 and pulse-wave extracting unit 22 are an example of the detector detecting heartbeat information of a subject. However, the function of the detector need not be divided between the image capturing unit 10 and information terminal 5. For example, the image capturing unit 10 may have the functions of the facial recognition unit 21 and pulse-wave extracting unit 22, or may be included in the information terminal 5.

FIGS. 4(A) to 4(C) are graphs for explaining how to determine the presence of the negative feeling based on a pulse wave. FIG. 4(A) shows an example of the waveform of a pulse-wave signal PW. The abscissa t and ordinate A thereof represent time (milliseconds) and intensity of amplitude of the pulse wave, respectively. As shown in FIG. 4(A), the pulse-wave signal PW is a substantially triangular wave reflecting variations in blood flow resulting from a heartbeat. Intervals between peaks P1 to Pn of the blood flow are denoted by pulse intervals dl to dn.

The interval calculating unit 23 detects the peaks P1 to Pn of the pulse-wave signal PW of the subject HK, uses the timepiece 50 to calculate the pulse intervals dl to dn in milliseconds, and further makes them time-series data.

The pulse-wave memory 24 stores the pulse intervals dl to dn detected by the interval calculating unit 23 as time-series data of pulse intervals.

FIG. 4(B) is a graph showing an example of variations in pulse intervals. This graph is called a Lorentz plot, and is made by plotting the time-series data of pulse intervals at coordinates (dn,dn−1) for n=1, 2, . . . ; the abscissa and ordinate represent pulse intervals dn and dn−1 (both in milliseconds), respectively. Since it is known that the degree of variations of dots in the graph of FIG. 4(B) reflects that of brain fatigue of the subject HK, showing the data scatter diagram of FIG. 4(B) on the display 41 allows for simply monitoring the degree of brain fatigue of the subject HK under measurement.

The chaotic analyzer 25 calculates a maximum Lyapunov exponent λ from the time-series data of pulse intervals stored in the pulse-wave memory 24, namely, coordinates (dn,dn−1) in the Lorentz plot of FIG. 4(B), by using the following Equation 1:

[Expression 1]

$$\lambda = \frac{1}{M}\sum_{k=1}^{M} \log_2 \frac{d(k)}{d(k-1)} \qquad \text{Equation 1}$$

where M denotes the sum of sampling times corresponding to the pulse intervals dl to dn, and d denotes the distance between patterns of time-series data at times k and k−1 (distance on the two-dimensional plane of the Lorentz plot). The chaotic analyzer 25 further outputs the calculated maximum Lyapunov exponent λ to the feeling determination unit 31 only when it receives data indicating that the measured values are valid from the measurement examining unit 26. The interval calculating unit 23 and chaotic analyzer 25 are an example of the calculating unit calculating a maximum Lyapunov exponent indicating the degree of variations in heartbeat intervals from the heartbeat information.

The measurement examining unit 26 determines whether the following two criteria are satisfied every time it receives the time-series signal E1 from the facial recognition unit 21, and outputs data indicating that the measured values are valid to the chaotic analyzer 25 if both criteria are satisfied. The first criterion is that a predetermined number of pieces of data of the time-series signal E1 are continuous, and that the amount of movement of the measurement frame Sa in the images Gr falls within a predetermined range; this is a criterion for determining whether the data is measured while the subject is resting. The second criterion is that there is no face in the images Gr except for the face of the subject HK; this is a criterion for confirming that there is no other person nearby.

The personal identification unit 27 refers to personal identification data previously registered in the detection device 1, based on the image data received from the facial recognition unit 21, to confirm the identity of the subject, and notifies the feeling determination unit 31 if it is confirmed.

FIG. 4(C) is a graph showing a relationship between the negative feeling and the maximum Lyapunov exponent indicating the degree of variations in heartbeat or pulse intervals. This graph is obtained by conducting a questionnaire survey on ten adult men and women to ask them how much they feel fatigued and whether they are so fatigued as to feel brain fatigue, anxiety or depression, measuring the maximum Lyapunov exponent $\lambda$ of pulse intervals for the same subjects, and graphically representing the relationship between the answers and values of $\lambda$. F0 to F4 correspond to "no fatigue," "fatigue appropriate to age," "temporary fatigue," "chronic fatigue" and "negative feeling," respectively. The ordinate of the graph represents the maximum Lyapunov exponent $\lambda$.

FIG. 4(C) shows that mere fatigue leads to a nearly-zero maximum Lyapunov exponent with small magnitude while a negative feeling leads to a negative maximum Lyapunov exponent with large magnitude. For these ten people, the threshold of the maximum Lyapunov exponent whether the subject has a negative feeling can be set at about −0.6, in consideration of variations in measurement.

The feeling determination unit 31 determines that the subject has a negative feeling if the maximum Lyapunov exponent $\lambda$ received from the chaotic analyzer 25 satisfies the following Equation 2, and that the subject does not have a negative feeling if $\lambda$ does not satisfy Equation 2:

$$\lambda \leq \lambda t \quad \text{Equation 2}$$

where the threshold $\lambda t$ is −0.6; however, it may be a different value depending on the characteristic required of the detection device 1. If it determines that the negative feeling occurs, the feeling determination unit 31 stores that result in the feeling data memory 32 in association with information on the measurement date and time and identifying information specific to the subject. At this time, the value of the maximum Lyapunov exponent $\lambda$ may also be stored in the feeling data memory 32. The feeling determination unit 31 is an example of the feeling determination unit determining whether the subject has a negative feeling with brain fatigue, anxiety or depression, based on the maximum Lyapunov exponent.

The MCI determining unit 33 counts frequency of occurrence of the negative feeling of the subject by the month separately for the morning and afternoon, based on the information stored in the feeling data memory 32. The MCI determining unit 33 then determines whether the subject suffers from MCI or not, as follows, based on patterns of occurrence of the negative feeling obtained by counting, in accordance with the criteria shown in Table 1.

If the number of occurrences of the negative feeling per month is 20 or less, then the subject is normal regardless of the times and period of occurrence.

If the negative feeling occurs only in the morning or afternoon regardless of the number of occurrences thereof, or if the number of occurrences of the negative feeling per month is 20 or more but it continues for less than three months, then the subject suffers from pseudodementia.

If the number of occurrences of the negative feeling per month is 20 or more in both the morning and afternoon and it continues for three months or more, then the subject suffers from MCI.

The number of occurrences of the negative feeling refers to that of times when measurements of the maximum Lyapunov exponent $\lambda$ satisfy above Equation 2. Since the criteria of the number, period or duration, and times of occurrences of the negative feeling shown in Table 1 are merely an example, other values may be employed depending on the characteristic required of the detection device 1. The MCI determining unit 33 is an example of the change determination unit determining whether the positive or negative feeling of the subject has changed, based on frequency of occurrence of the negative feeling in a predetermined period (period of three months or more in the example of Table 1).

TABLE 1

|  | the number of occurrences of the negative feeling | times when the netagive feeling occurs |
|---|---|---|
| normal | 20 or less per month regardless of its period | — |
| pseudo-dementia | — | in the morning or afternoon regardless of the number of occurrences per month |
| MCI | 20 or more per month but continuing for less than three months | — |
|  | 20 or more per month for three or more consecutive months | 20 or more per month in both the morning and afternoon |

The notifying unit 40 causes the result of determination by the MCI determining unit 33 to appear on the display 41. In particular, if the MCI determining unit 33 determines that the subject suffers from MCI, the notifying unit 40 causes a warning thereof to appear on the display 41 and transmits it to the outside via the transmitting unit 42. The notifying unit 40 is an example of the output unit outputting a result of determination by the change determination unit.

FIGS. 5(A) to 5(D) are graphs showing examples of a display screen of the detection device 1. FIGS. 5(A) to 5(D) show results obtained by applying the detection device 1 to a normal subject, a pseudodemential subject, another pseudodemential subject and an MCI subject, respectively. These graphs are shown on the display 41. The abscissas M thereof represent months during which the detection device 1 is applied; "1" and "8" indicate the first and last months of application, respectively. The ordinates N represent the numbers of occurrences of the negative feeling per month;

the hollow and solid bars indicate the numbers of occurrences thereof in the morning (AM) and afternoon (PM), respectively.

Figure 5:
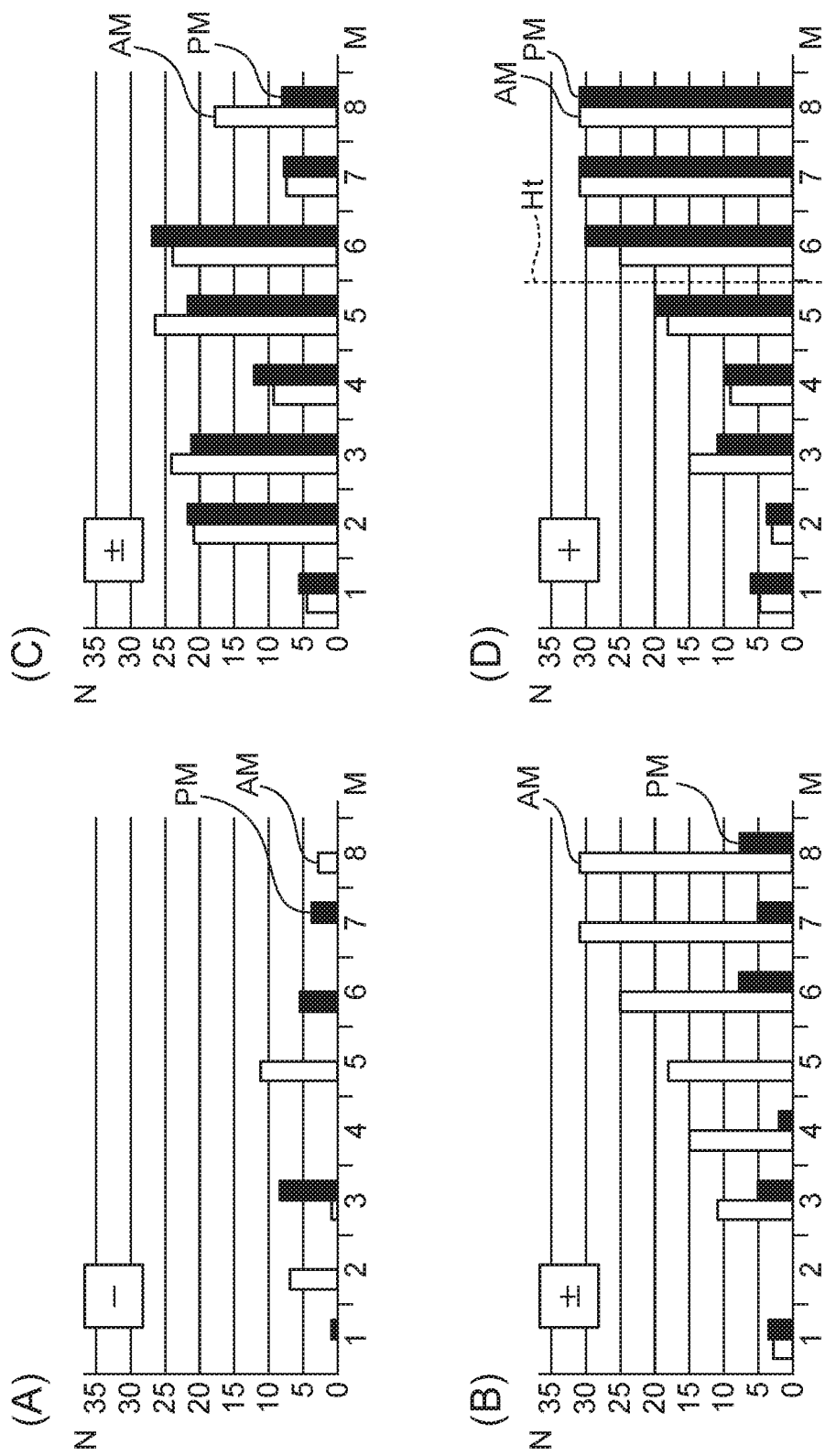
FIGS. 5(A) to 5(D) are graphs showing examples of a display screen of detection results by the detection device 1.

In the example of FIG. 5(A), the numbers of occurrences of the negative feeling are less than 20 from the first to last months of application. Since this fits the criterion of "normal" shown in Table 1, the detection device 1 displays "−" indicating normal, at the upper left of the graph.

In the example of FIG. 5(B), the numbers of occurrences of the negative feeling are less than 20 from the first to fifth months of application, and more than 20 from the sixth to last months thereof only in the morning. Since this fits one of the criteria of "pseudodementia" shown in Table 1, i.e., "in the morning or afternoon regardless of the number of occurrences per month," the detection device 1 displays "±" indicating pseudodementia, at the upper left of the graph.

In the example of FIG. 5(C), although the numbers of occurrences of the negative feeling are more than 20 in both the morning and afternoon in some months, it does not continue for three months. Since this fits the other criterion of "pseudodementia" shown in Table 1, i.e., "20 or more per month but continuing for less than three months," the detection device 1 displays "±" similarly to the case of FIG. 5(B).

In the example of FIG. 5(D), the numbers of occurrences of the negative feeling are more than 20 in both the morning and afternoon for three consecutive months from the sixth to last months of application. Since this fits the criterion of "MCI" shown in Table 1, i.e., "20 or more per month for three or more consecutive months" and "20 or more per month in both the morning and afternoon," the detection device 1 displays "+" indicating MCI, at the upper left of the graph.

Figure 6:
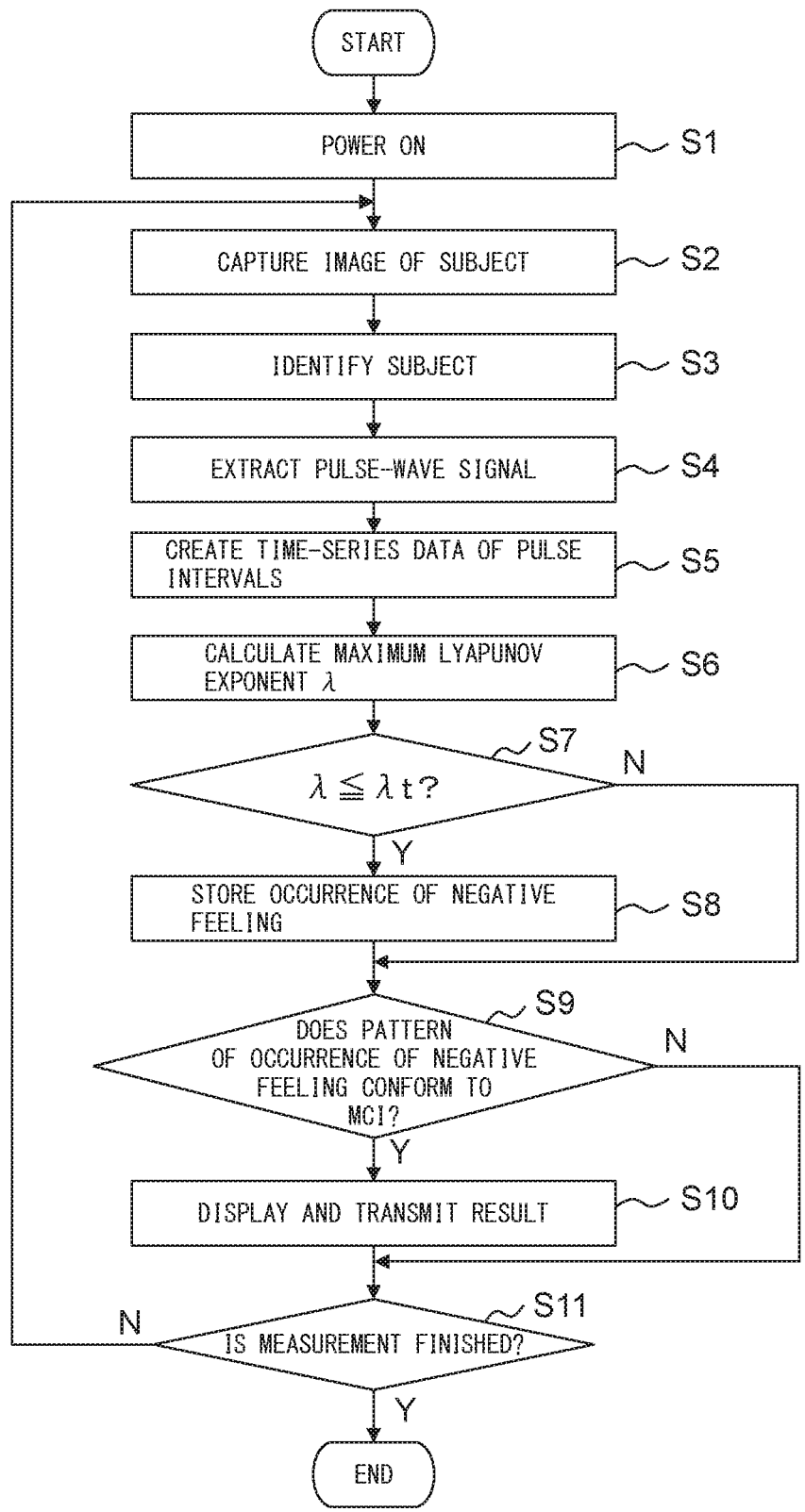
FIG. 6 is a flowchart showing an operational example of the detection device 1.

FIG. 6 is a flowchart showing operations of the detection device 1. First, when turned on by a user, the information terminal 5 turns on the image capturing unit 10 through radio waves RW (S1). After the detection device 1 is thus turned on, the image capturing unit 10 captures images Gr of a measurement frame Sa of a subject HK with the image sensor 11, and transmits the image data to the information terminal 5 (S2). Subsequently, the facial recognition unit 21 selects a measurement region based on the image data of the subject HK, while the personal identification unit 27 identifies the subject HK (S3). The pulse-wave extracting unit 22 extracts a pulse-wave signal of the subject HK from the time-series signal E1 of skin color of the measurement region selected by the facial recognition unit 21 (S4). The interval calculating unit 23 calculates pulse intervals from the pulse-wave signal of S4 to create time-series data thereof, and stores the data in the pulse-wave memory 24 (S5).

Next, the chaotic analyzer 25 calculates the maximum Lyapunov exponent $\lambda$ of pulse intervals, based on the time-series data of pulse intervals stored in S5 (S6). The feeling determination unit 31 compares that value with the threshold $\lambda t$ (S7). If $\lambda$ is not more than $\lambda t$ (Yes in S7), it determines that the negative feeling occurs, and stores that result in the feeling data memory 32 in association with information on the measurement date and time (S8).

Further, the MCI determining unit 33 counts frequency of occurrence of the negative feeling by the month, and determines which criterion of normal, pseudodementia and MCI the counted values satisfy (S9). If it is determined in S9 that the subject suffers from MCI (Yes in S9), the notifying unit 40 causes a warning thereof to appear on the display 41 and transmits it to the outside via the transmitting unit 42 (S10). Thereafter, the information terminal 5 determines whether the measurement of the subject by the image capturing unit 10 is continued or stopped (S11). If continued (No in S11), the process returns to S2; if stopped (Yes in S11), the information terminal 5 stops the operations of the image capturing unit 10 and terminates the process.

Since the detection device 1 uses the image capturing unit 10 to measure pulse waves without touching the subject and being noticed by him/her, the subject HK does not feel stress of measurement. For example, when a photoelectric sensor is used to measure a pulse (sphygmus), the constraint that the subject should keep a fingertip constantly touching the sensor causes stress on the subject, which may affect results of measurement; however, the detection device 1 does not cause such a problem. The detection device 1 can automatically conduct measurements only by the image capturing unit 10 being placed beside the subject HK, and thus does not restrict movements of the subject. Further, real-time measurement is not necessary, and determination of MCI can be made later by using video data captured by the image sensor 11. Thus, pulse-wave signals can be obtained while the subject is relaxed and not conscious of the measurement.

The detection device 1 can surely and correctly detect normal, pseudodementia and MCI, and make time-varying changes in psychiatric disorder of the subject be easily grasped. In particular, the detection device 1 can quantify frequency of occurrence of the negative feeling in the morning and afternoon, which characterizes MCI, and thus can distinguish MCI from pseudodementia, which is caused by senile depression and looks very similar to MCI. For example, in the example shown in FIG. 5(D), it can be presumed that the subject developed MCI at a time Ht between the fifth and sixth months of application. The detection device 1 is thus useful for clinical diagnosis of MCI.

Figure 7:
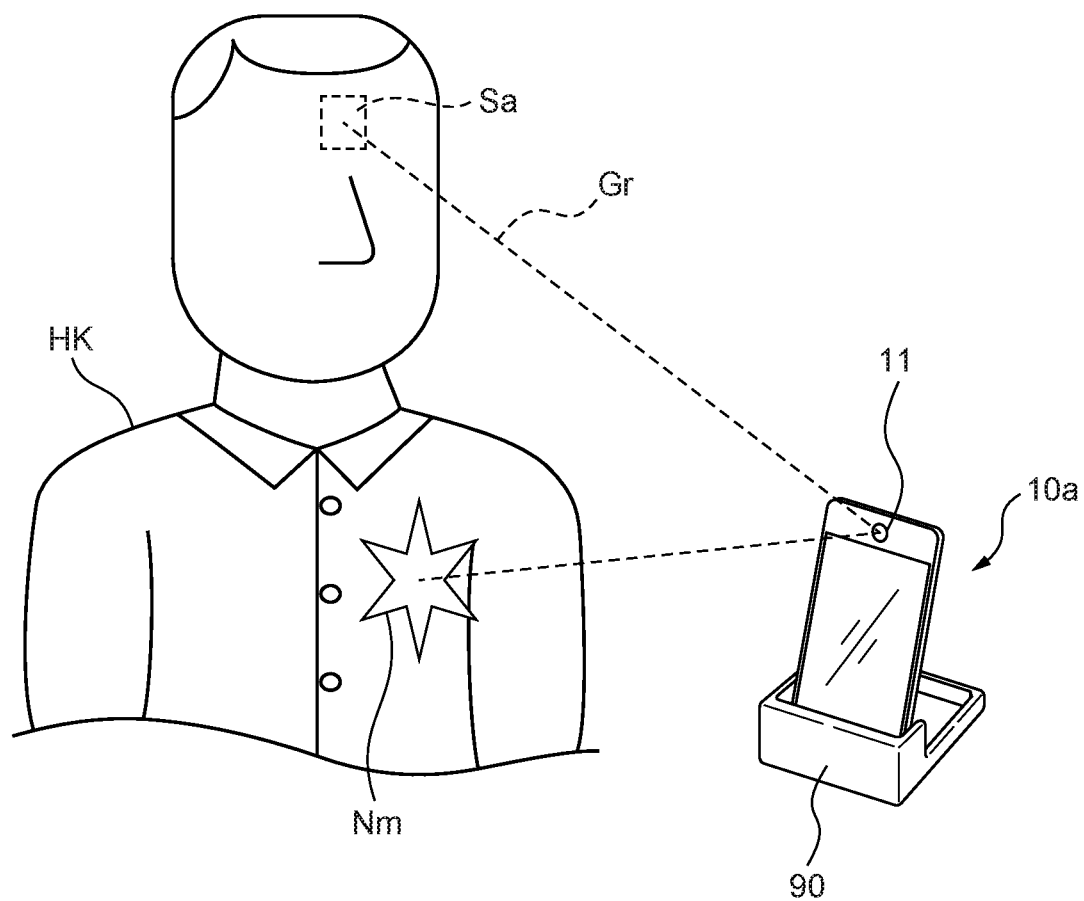
FIG. 7 is a perspective view showing the detection device 1 including an image capturing unit 10a in use.

FIG. 7 is a perspective view showing the detection device 1 including an image capturing unit 10a in use. The image capturing unit 10a differs from the image capturing unit 10 of FIG. 1 in that the function of personal identification is added. When the image capturing unit 10a is used, subjects respectively wear personal identification marks with different shapes on their chests, for example, as shown in FIG. 7. Although the subject HK in the illustrated example wears a star-shaped personal identification mark Nm, the marks may include letters or symbols thereon. The image capturing unit 10a identifies, by image recognition, the personal identification mark Nm in the images Gr captured by the image sensor 11, and identifies the subject HK to be measured out of previously registered people, and thereafter transmits identifying information of the subject HK and the images Gr of the measurement frame Sa, as a data set, to the information terminal 5.

Use of the image capturing unit 10a allows for individually identifying subjects and detecting their MCI. Thus, it is possible to share the detection device 1 with people in a nursing home, for example, which allows for efficient and low-cost detection of MCI.

It is known that aerobic exercise and cognitive therapy, such as keeping a diary about activities, are effective in preventing the cognitive function from declining. However, only few of middle-aged and elderly people can put aerobic exercise and cognitive therapy into practice. A method for preventing senile dementia which everybody can put into practice at the stage of MCI and a method for remedying MCI are not known yet. Although the detection device 1 can detect MCI, it is preferred that it have not only the detecting function but also an additional function which everybody can put into practice and prevent appearance of senile dementia at the stage of MCI.

In recent years, mindfulness-based stress reduction (MBSR) and mindfulness-based cognitive therapy (MBCT), which are methods for remedying brain functions, have been applied to medical treatment. Mindfulness refers to a psychological process where the attention is focused on current internal and external experiences. Since the state of mindfulness leads to conversion from a negative feeling to a positive feeling (state without brain fatigue, anxiety and depression, or state where the maximum Lyapunov exponent indicating the degree of variations in heartbeat intervals is 0 or positive), the above techniques, if correctly conducted, have the effect of remedying brain functions. However, since achieving mindfulness requires a contemplative technique and other training which are practiced under subjective coaching, it is difficult for people who practice them to realize the effect thereof and to practice them correctly.

To address this, a description will be given below of a device which makes use of mindfulness therapy in combination with the MCI determining function of the detection device 1 and can be passively used by non-handicapped or MCI-stage persons to prevent senile dementia from progressing.

Figure 8:
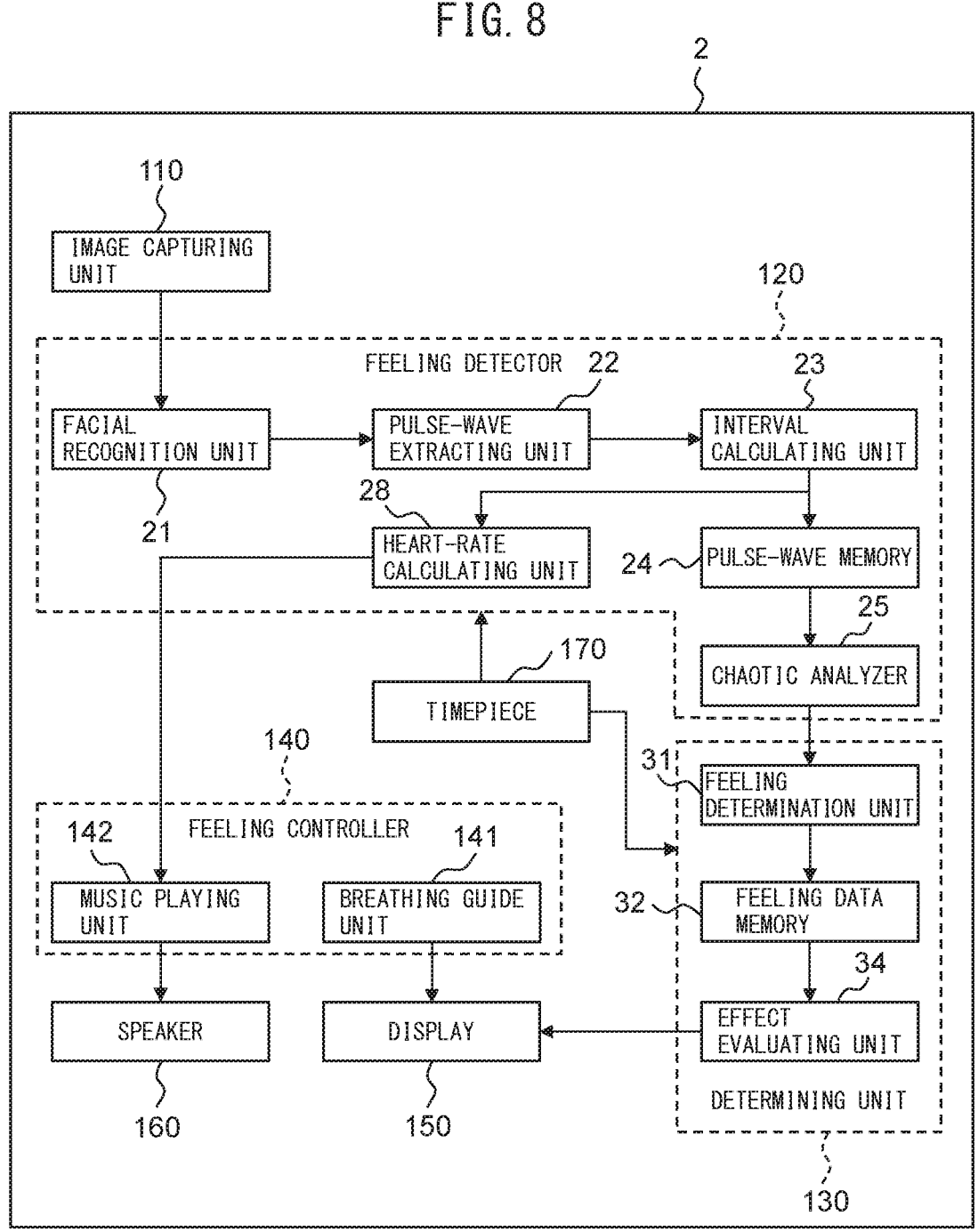
FIG. 8 is a block diagram of a prevention device 2.

FIG. 8 is a block diagram of a prevention device 2. The prevention device 2, which is an example of the detection device, is a smartphone or tablet device, for example, and includes an image capturing unit 110, a feeling detector 120, a determining unit 130, a feeling controller 140, a display 150, a speaker 160 and a timepiece 170. The prevention device 2 conducts feeling control on a user by breathing guidance and music playback to cause the user to concentrate so that the brain converts into the state of mindfulness (namely, conversion from the negative to positive feeling), and feeds changes in positive and negative feelings during the feeling control (guidance) back to the user.

The image capturing unit 110 captures images of an exposed portion of user's skin, similarly to the image capturing unit 10 in the detection device 1, in order to detect a pulse wave of the user. The image capturing unit 110 is incorporated into the prevention device 2, but may be separated from the prevention device, such as a tablet device, as in the detection device 1. Alternatively, a sensor detecting an electrocardiogram or pulse wave of the user may be used instead of the image capturing unit 110.

The feeling detector 120 includes a facial recognition unit 21, a pulse-wave extracting unit 22, an interval calculating unit 23, a pulse-wave memory 24 and a chaotic analyzer 25, which are the same as those in the detection device 1, and calculates the maximum Lyapunov exponent of pulse intervals at intervals of several tens of seconds, for example, during the guidance by the feeling controller 140. The feeling detector 120 of the prevention device 2 further includes a heart-rate calculating unit 28 which calculates the user' heart rate (pulse rate) at regular intervals from the pulse intervals obtained by the interval calculating unit 23, similarly to the calculation of the maximum Lyapunov exponent.

The determining unit 130 includes a feeling determination unit 31, a feeling data memory 32 and an effect evaluating unit 34. The feeling determination unit 31 and feeling data memory 32 are the same as those in the detection device 1. However, the feeling determination unit 31 of the prevention device 2 determines that the user has a positive feeling if the maximum Lyapunov exponent λ received from the chaotic analyzer 25 does not satisfy Equation 2. Further, the feeling determination unit 31 causes the user' feeling (negative or positive feeling) determined by the feeling determination unit 31 during the guidance by the feeling controller 140 to appear on the display 150. Alternatively, the feeling determination unit 31 may classify the user' feeling into four categories, such as "positive feeling (free of stress)," "active," "slightly negative feeling (slight fatigue)" and "negative feeling (fatigue)," depending on the value of the maximum Lyapunov exponent λ, and cause the category into which the user falls to be displayed.

The effect evaluating unit 34 is an example of the change determination unit, and determines whether the positive or negative feeling of the user has changed in the period (guidance period) during which the feeling controller 140 continues the guidance. To this end, the effect evaluating unit 34 refers to the feeling data memory 32 to calculate the rate of occurrence of the positive feeling in the guidance period, and causes that value to appear on the display 150 as the degree of achievement of mindfulness (degree of improvement from the negative to positive feeling) by use of the prevention device 2. The rate of occurrence of the positive feeling is a value defined as "(the number of times when the result of determination is the positive feeling)/(the number of determinations by the feeling determination unit 31)". In other words, the effect evaluating unit 34 evaluates how much the user's feeling has been positively changed by using the prevention device 2, and feeds it back to the user.

The feeling controller 140 includes a breathing guide unit 141 and a music playing unit 142, and makes the user be peaceful and concentrate on breathing and music, thereby leading the user to the positive feeling.

Figure 9:
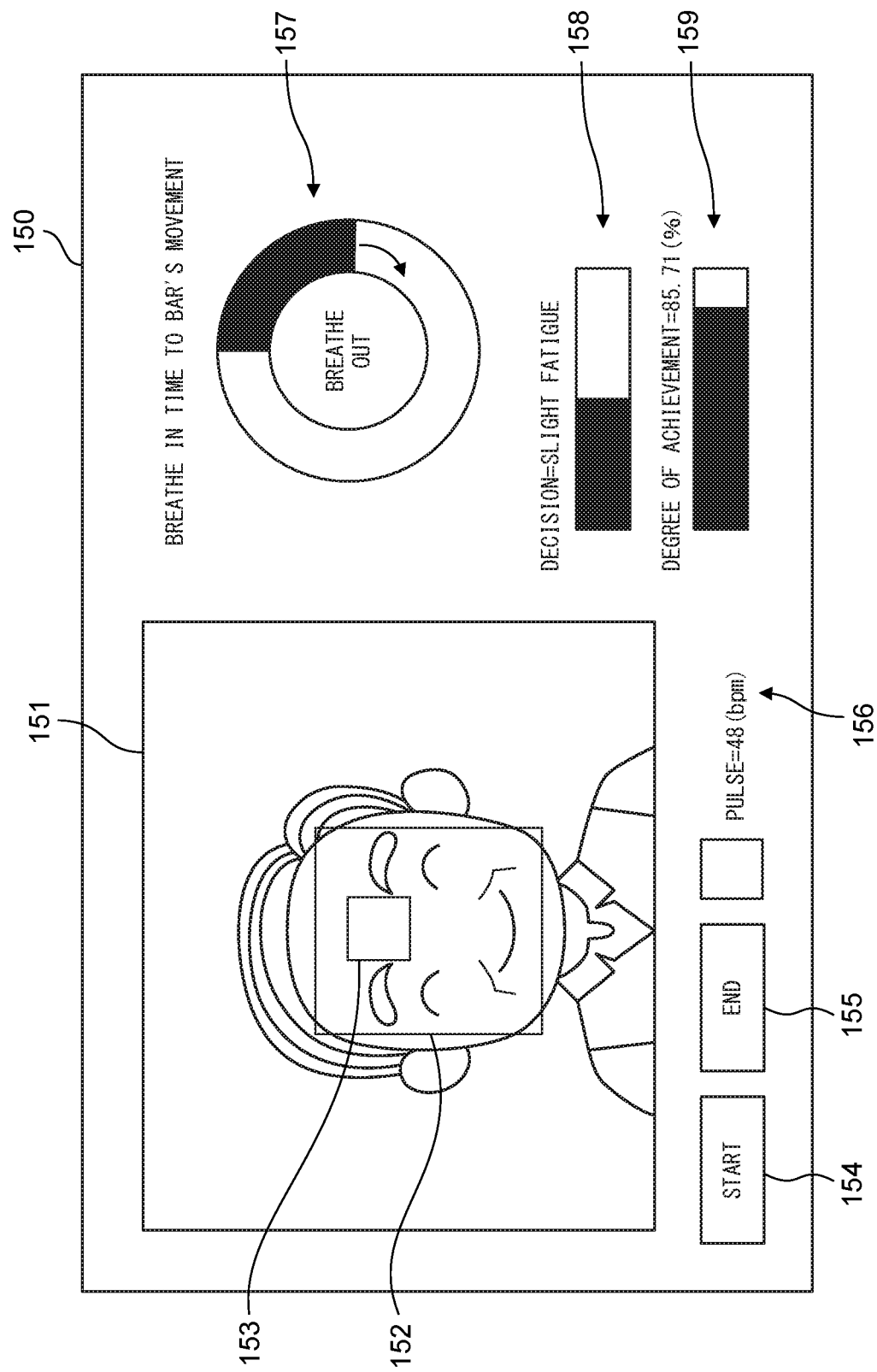
FIG. 9 is a diagram showing an example of a display screen of the prevention device 2.

The breathing guide unit 141 prompts the subject to draw a deep breath such that exhalation is slower than inhalation, thereby causing the subject to concentrate on breathing. Fast inhalation and slow exhalation stimulate the diaphragm and consequently calm the autonomic nerves, which have the effect of changing feelings positively. This deep breath is preferably a deep breath with prolonged exhalation such that the exhalation period is two or three times as long as the inhalation period, e.g., two-second inhalation and six-second exhalation. The breathing guide unit 141 thus notifies the subject of timings of the inhalation and exhalation with a screen of the display 150. At this time, for example, a bar whose length gradually changes from the start to end of the inhalation and exhalation periods may be displayed, as shown in FIG. 9 described later. Since humans have the habit of focusing on a moving or changing object, following such a changing bar with eyes causes the subject to concentrate on the display or breathing, which makes the subject be peaceful without thinking about the negative feeling.

The music playing unit 142 plays music including a phrase longer than the period of breathing, thereby causing the user to concentrate on the music. The piece of music played by the music playing unit 142 is one having a phrase period longer than the period of breathing guided by the breathing guide unit 141. This is because a phrase period shorter than the period of guided breathing makes the breathing synchronize not with the bar shown on the display 150 but with the music, which reduces the effect of the breathing guidance.

In addition to this condition of the phrase period, the piece of music played by the music playing unit 142 preferably satisfies at least one of the following conditions.

(1) The beat of the music has a frequency of 4 to 6 kHz.
(2) The scale of the music has a frequency distribution centered on 528 Hz.
(3) The sensual BPM (beats per minute) of the tempo of the music coincides with the BPM of the resting heart rate.

Pieces of music allegedly effective in calming autonomic nerves satisfy these conditions in common. Condition (1) is because the frequency of beat sound which is easily resonant with the backbone and brainstem is 4 to 6 kHz. Condition (2) is because the cells are said to self-repair at a frequency of 528 Hz. Condition (3) is because coincidence of the heartbeat and the tempo of the music is likely to provide peace of mind.

In order to satisfy condition (3), the music playing unit 142 may control the tempo of the music according to the heart rate of the subject calculated from the heartbeat information. To this end, the music playing unit 142 may obtain the user's heart rate (pulse rate) from the heart-rate calculating unit 28, and adjust the tempo of playback of the music so that it matches the heart rate. For example, for a piece of music in triple time, the sensual tempo is 0.66 times as fast as the physical tempo (actual tempo); thus, if the actual tempo is 101.68 BPM, the sensual tempo is 66.9 BPM. Since the average resting heart rate of adults is about 65 BPM, in playing a piece of music whose actual tempo is 101.68 BPM, the music playing unit 142 may make fine adjustments to the tempo of playback thereof according to the heart rate.

The display 150 is an example of the output unit. During the guidance by the feeling controller 140, the display 150 regularly shows which of the negative and positive feelings the result of determination by the feeling determination unit 31 is, and after the guidance, it shows the rate of occurrence of the positive feeling (degree of achievement) calculated by the effect evaluating unit 34. The display 150 thereby makes the user realize the feeling during use and the effect of changing feelings after use.

The speaker 160 is used when the music playing unit 142 plays music. The user may listen to the music with headphones; in this case, the prevention device 2 may include an earphone jack instead of the speaker 160. The timepiece 170 is the same as the timepiece 50 in the detection device 1.

FIG. 9 is a diagram showing an example of a display screen of the prevention device 2. As shown in FIG. 9, the display 150 shows a user's face image 151 captured by the image capturing unit 110 on the left side of the screen, for example. Reference numerals 152, 153 indicate the face region recognized by the facial recognition unit 21 and the measurement frame for extracting pulse waves, respectively. Buttons 154, 155 for inputting instructions to start and end the measurement are shown at the lower left of the screen. The user's pulse rate calculated by the heart-rate calculating unit 28 is shown on the right thereof (reference numeral 156).

A circular progress bar 157 for the breathing guidance by the breathing guide unit 141 is shown on the upper right of the screen. For example, in the inhalation period, the black region of this bar extends clockwise from the 12 o'clock position as indicated by an arrow in the figure with the passage of time to fill all the circle, and in the next exhalation period, it also extends similarly. The shape of such a bar is not limited to circular, but may be straight, for example. The user's feeling determined by the feeling determination unit 31 is shown at the lower right of the screen (reference numeral 158); this part of the screen is updated at regular (e.g., 40-second) intervals. Further, the rate of occurrence of the positive feeling (degree of achievement) calculated by the effect evaluating unit 34 also appears at the lower right of the screen (reference numeral 159), after the breathing guidance by the breathing guide unit 141 and the music playback by the music playing unit 142.

Figure 10:
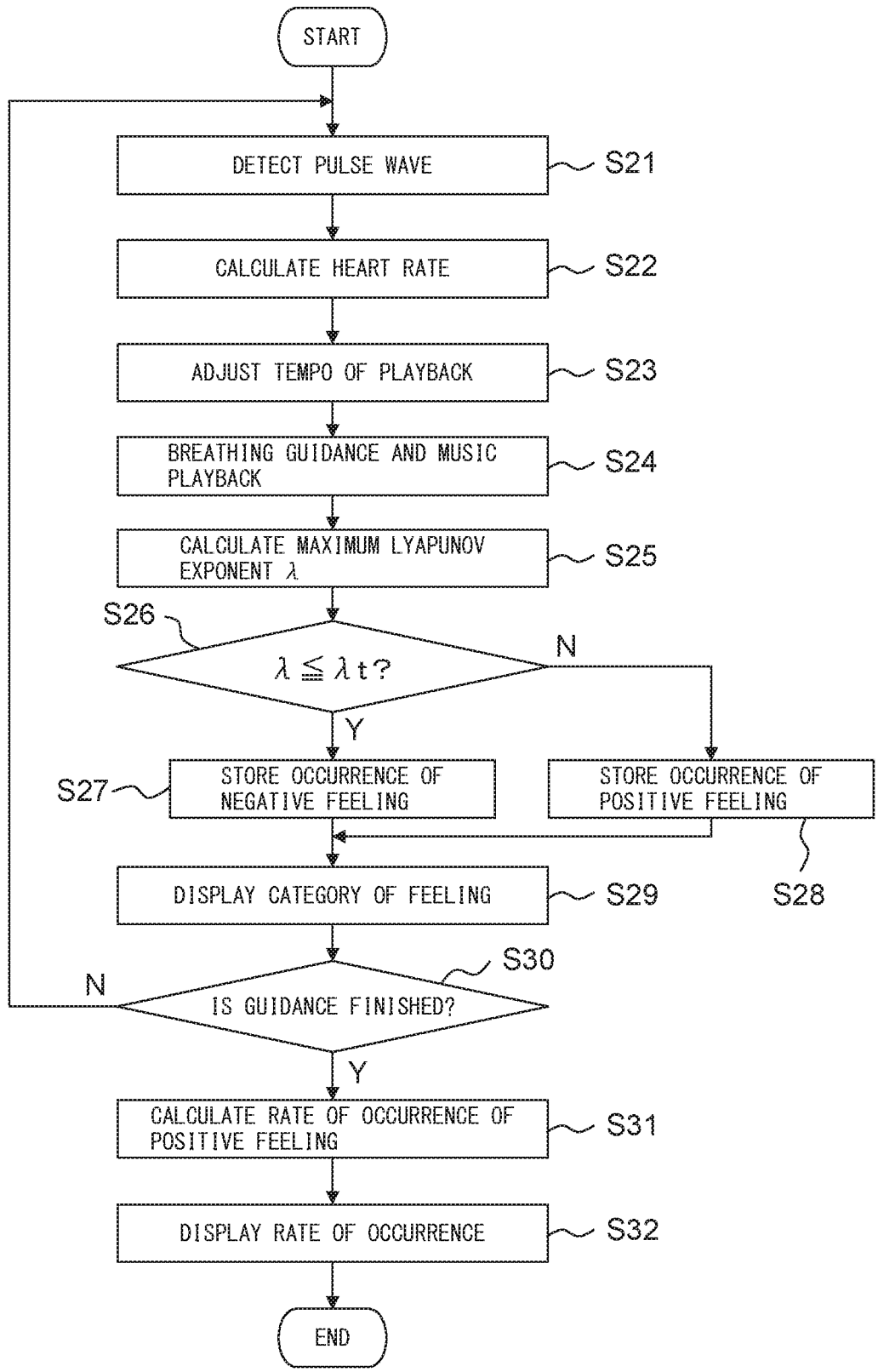
FIG. 10 is a flowchart showing an operational example of the prevention device 2.

FIG. 10 is a flowchart showing an operational example of the prevention device 2. First, the image capturing unit 110 and feeling detector 120 detect a pulse wave of the user, similarly to the detection device 1 (S21). The heart-rate calculating unit 28 calculates the user's heart rate from the pulse intervals (S22). The music playing unit 142 adjusts the tempo of playback of music so that it matches the heart rate calculated in S22 (S23). The breathing guide unit 141 and music playing unit 142 then conduct the breathing guidance and music playback (S24). At the same time, the chaotic analyzer 25 calculates the maximum Lyapunov exponent $\lambda$ from the pulse wave detected in S21 (S25), while the feeling determination unit 31 compares that value with the threshold $\lambda t$ (S26).

The feeling determination unit 31 determines that the negative feeling occurs if $\lambda$ is not more than $\lambda t$ (Yes in S26), and that the positive feeling occurs if $\lambda$ is larger than $\lambda t$ (No in S26), and stores that result in the feeling data memory 32 (S27, 28). Subsequently, the feeling determination unit 31 determines which of the categories "positive feeling," "active," "slightly negative feeling" and "negative feeling" the user's feeling falls into, depending on the value of the maximum Lyapunov exponent $\lambda$, and causes that category to appear on the display 150 (S29). The feeling detector 120 then determines whether the guidance by the breathing guide unit 141 and music playing unit 142 is finished (S30). If the guidance is not finished (No in S30), the process returns to S21. If finished (Yes in S30), the effect evaluating unit 34 calculates the rate of occurrence of the positive feeling (degree of achievement) (S31), causes that value to appear on the display 150 (S32), and terminates the process.

Figure 11:
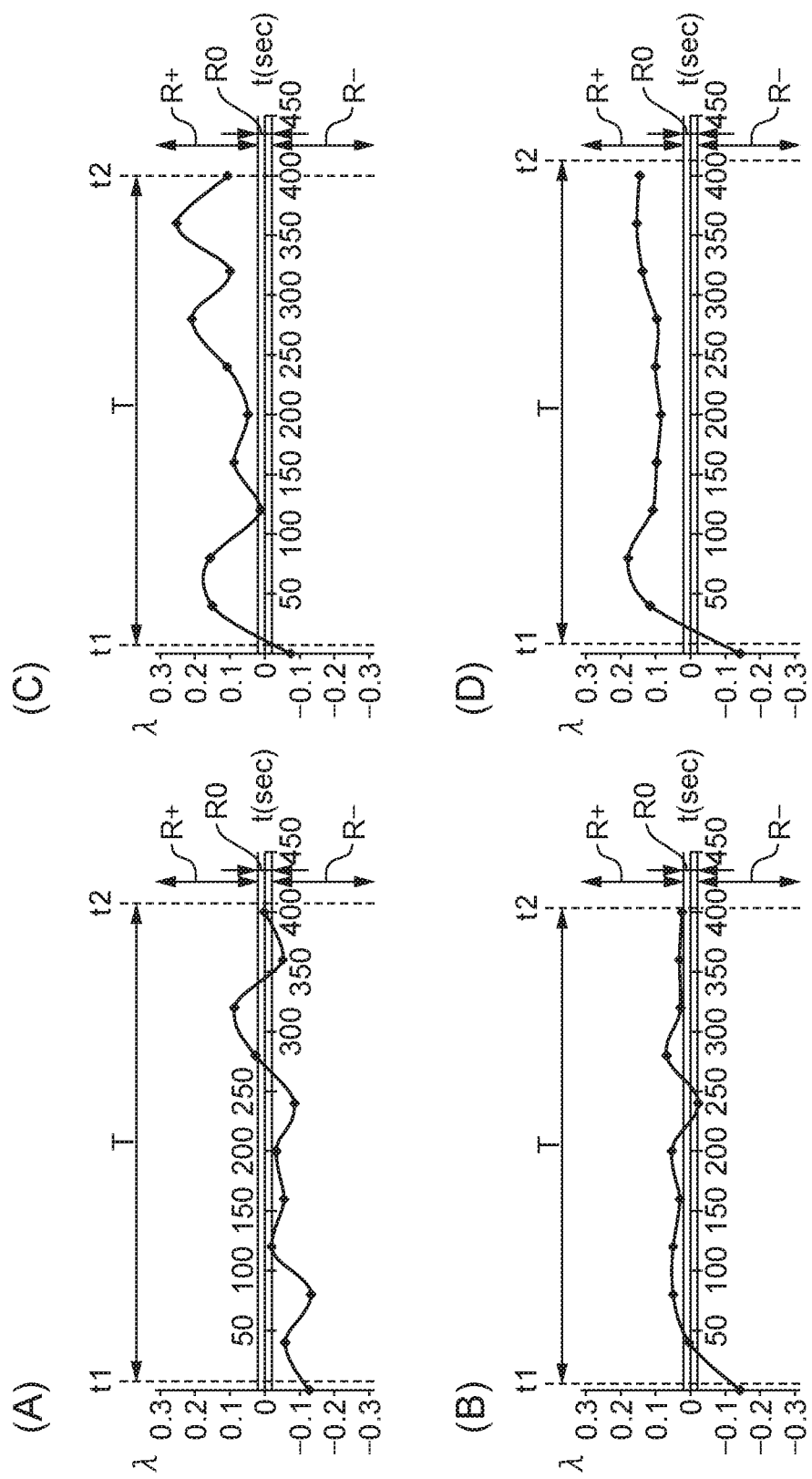
FIGS. 11(A) to 11(D) are graphs showing the difference in changes in positive and negative feelings depending on the presence or absence of the feeling control.

FIGS. 11(A) to 11(D) are graphs showing the difference in changes in positive and negative feelings depending on the presence or absence of the feeling control. The abscissas t and ordinates $\lambda$ of the graphs represent time (seconds) and the maximum Lyapunov exponent, respectively. The regions R+ ($\lambda > 0$) and R− ($\lambda < 0$) in the graphs correspond to the positive and negative feelings, respectively. The region R0 ($\lambda \approx 0$) therebetween corresponds to a feeling intermediate between the positive and negative feelings. FIGS. 11(A) to 11(D) show variations over time in feelings of a user having a negative feeling at time 0, and correspond to cases without the breathing guidance and music playback, only with the music playback, only with the breathing guidance, and with both the breathing guidance and music playback, respectively. In FIGS. 11(B) to 11(D), the feeling control is conducted during the period T from times t1 to t2.

In the examples of FIGS. 11(A) to 11(D), of ten feeling determinations, the numbers of times when the result of determination is the positive feeling are two, eight, nine and ten, respectively, and thus the rates of occurrence thereof are 20%, 80%, 90% and 100%, respectively. FIG. 11(A) shows that the negative feeling is substantially maintained without the feeling control, while FIGS. 11(B) to 11(D) show that the negative feeling is converted to the positive feeling by the feeling control. This improvement effect is more noticeable in the cases of FIGS. 11(C) and 11(D) with the breathing guidance than in the case of FIG. 11(B) only with the music playback. In particular, as shown in FIG. 11(D), conducting both the breathing guidance and music playback allows the positive feeling to be maintained longer, and has the highest effect of changing feelings.

As described above, it is preferred to conduct both the breathing guidance and music playback as the feeling control. However, since the effect of changing feelings can be produced only by one of the breathing guidance and music playback, the prevention device 2 may include only one of the breathing guide unit 141 and music playing unit 142 as the feeling controller.

The prevention device 2 can be used by everybody, since the user is only required to sit in front of the device and to breathe about 15 to 20 minutes a day, for example, in accordance with the displayed bar while listening to the played music. The prevention device 2 displays the rate of occurrence of the positive feeling during use as the degree of achievement of mindfulness, which makes the user easily realize its effect and be motivated to use it.

Other than the breathing guidance and music playback, it is said that light work which can be done only with a hand, such as coloring in line drawings (coloring book), is effective in preventing senile dementia, since a person who does such work can concentrate thereon without thinking anything. However, since too difficult or too easy light work may lead to an inadequate or opposite effect, its degree of difficulty should be suitable for each user. Further, even if the degree of difficulty of light work is appropriate, it is difficult for a user to realize its effect and to be motivated to do such work. To address this, a description will be given below of a device which has the function of assigning a task involving light work in combination with the MCI determining function of the detection device 1, makes a user voluntarily work on the task and thereby has the effect of changing feelings to prevent senile dementia.

Figure 12:
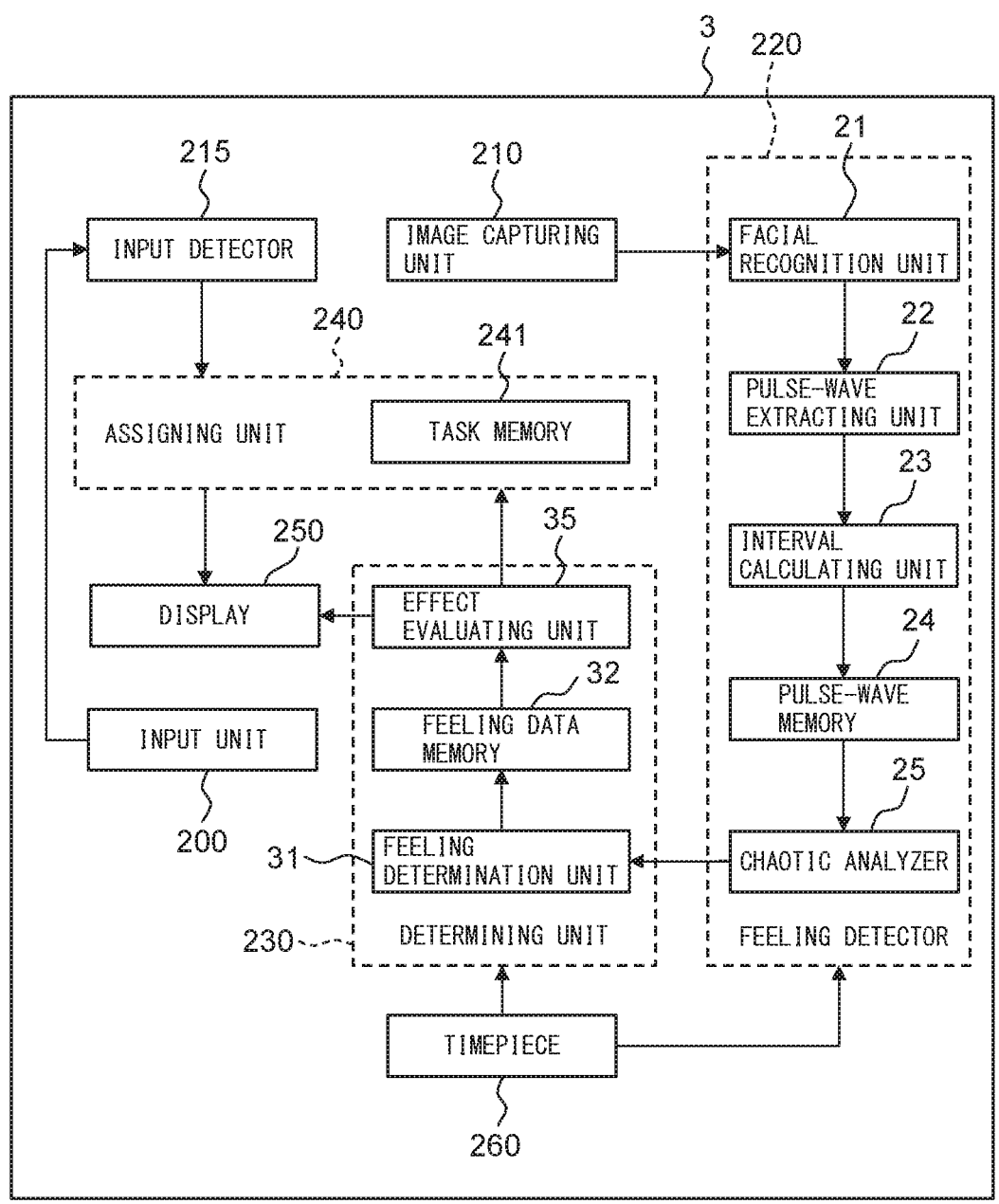
FIG. 12 is a block diagram of a prevention device 3.

FIG. 12 is a block diagram of a prevention device 3. The prevention device 3, which is an example of the detection device, is a smartphone or tablet device, for example, and includes an input unit 200, an image capturing unit 210, an input detector 215, a feeling detector 220, a determining unit 230, an assigning unit 240, a display 250 and a timepiece 260. The prevention device 3 shows a task on the display 250, makes the user do light work which requires processing an object displayed as the task via the input unit 200, and thereby changes the user's feeling positively and feeds the effect of the light work back to the user.

The input unit 200 is a stylus or mouse, and is used for input by the user. The image capturing unit 210 captures images of an exposed portion of user's skin, similarly to the image capturing unit 110 in the prevention device 2, in order to detect a pulse wave of the user. The input unit 200 may be a mouse including a built-in pulse-wave sensor, which may be used instead of the image capturing unit 210.

The input detector 215 detects the amount of input by the user using the input unit 200. In other words, the input detector 215 detects (counts) the number of movements required for the user's operations on objects, such as figures, shown on the display 250 while the task is assigned. The amount of input (the number of movements) refers to, for example, the number of changes of coordinates of the stylus or mouse, which is the input unit 200, per unit time.

The feeling detector 220 includes a facial recognition unit 21, a pulse-wave extracting unit 22, an interval calculating unit 23, a pulse-wave memory 24 and a chaotic analyzer 25, which are the same as those in the detection device 1, and calculates the maximum Lyapunov exponent of pulse intervals at intervals of several tens of seconds, for example, while a task is assigned by the assigning unit 240 (during light work).

The determining unit 230 includes a feeling determination unit 31, a feeling data memory 32 and an effect evaluating unit 35. The feeling determination unit 31 and feeling data memory 32 are the same as those in the prevention device 2.

The effect evaluating unit 35 is an example of the change determination unit, determines whether the positive or negative feeling of the user has changed in the period (working time from the start to end of the work) during which the assigning unit 240 assigns a task. To this end, the effect evaluating unit 35 calculates the rate of occurrence of the positive feeling in the working time, and causes that value to appear on the display 250 as the rate of occurrence of the positive feeling (degree of improvement from the negative to positive feeling) by use of the prevention device 3, similarly to the effect evaluating unit 34 in the prevention device 2. In other words, the effect evaluating unit 35 evaluates how much the user's feeling has been positively changed by using the prevention device 3, and feeds it back to the user.

The assigning unit 240 includes a task memory 241 storing multiple tasks, selects one of the tasks and causes it to appear on the display 250. These tasks each require input of the user for processing an object shown on the display 250, and vary in degree of difficulty.

FIGS. 13(A) to 13(F) are diagrams showing examples of tasks assigned by the prevention device 3. For example, the assigning unit 240 assigns, as the task, a coloring task which requires coloring in regions divided by lines shown on the display 250, or a handwriting task which requires copying letters shown on the display onto the display by hand. FIGS. 13(A) to 13(C) shows examples of the coloring task, while FIGS. 13(D) to 13(F) shows examples of the handwriting task. For example, in the coloring tasks, the user moves a mouse to color in the regions, while in the handwriting tasks, the user traces the displayed letters with a stylus.

The coloring tasks increase in difficulty in the order of FIGS. 13(A), 13(B) and 13(C), while the handwriting tasks increase in difficulty in the order of FIGS. 13(D), 13(E) and 13(F). For the coloring tasks, the degree of difficulty is defined as the number of lines per screen, the number of contours or the maximum density of lines, for example. The numbers of contours nL in the examples of FIGS. 13(A) to 13(C) are 5, 12 and about 65, respectively. For the handwriting tasks, the degree of difficulty is defined as the thickness of thin letters displayed as a guide, for example.

Appropriate tasks assigned by the assigning unit 240 are ones requiring working time from about several tens of seconds to several minutes, for example, and include origami (folding paper into a figure) and crossword puzzles, for example, other than coloring and handwriting (copying a sutra). In particular, coloring and handwriting are suitable for displaying on a tablet device, since they are easily digitized. However, for example, quizzes which can be answered in several seconds are not suitable as the task, since determination of feelings is difficult. Exercise involving movement of legs is not suitable for the task either, since it forbids determination of feelings based on heartbeat intervals. Thus, it is preferred that the tasks assigned by the assigning unit 240 be ones which the user can do only with a hand, without using the legs, while sitting.

Figure 14:
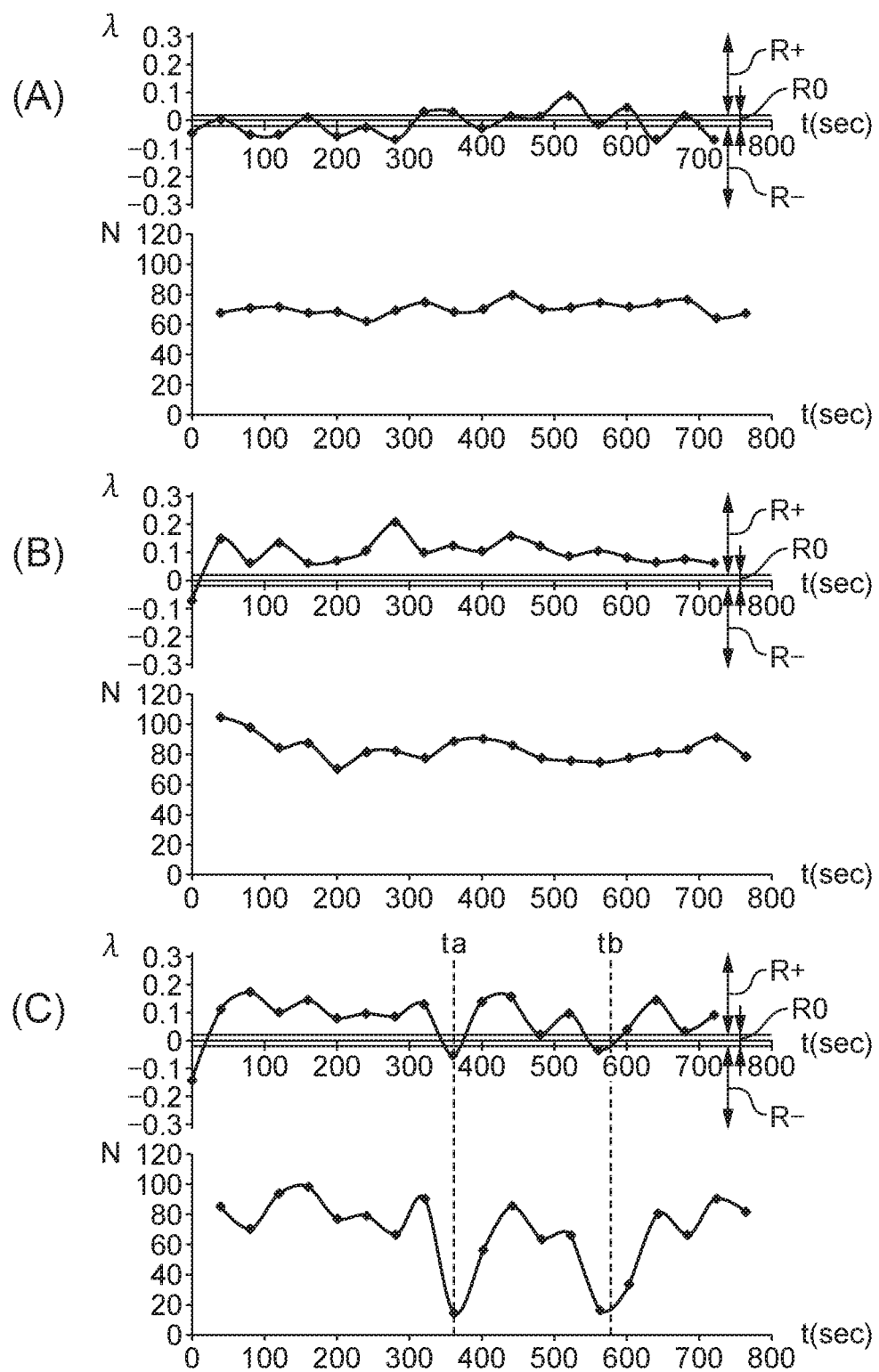
FIGS. 14(A) to 14(C) are graphs showing the differences in changes in positive and negative feelings and the amount of input depending on the degrees of difficulty of the tasks.

FIGS. 14(A) to 14(C) are graphs showing the differences in changes in positive and negative feelings and the amount of input depending on the degrees of difficulty of the tasks. The upper part of each figure shows variations over time in the maximum Lyapunov exponent calculated by the feeling detector 220 during light work of the user, while the lower part thereof shows the amount of input detected by the input detector 215. The abscissa t and ordinate λ, N of each figure represent time (seconds), and the maximum Lyapunov exponent and the amount of input, respectively. The regions R+, R−, R0 in the graphs correspond to the positive and negative feelings, and a feeling intermediate therebetween, respectively. FIGS. 14(A) to 14(C) show variations over time in feelings and the amount of input of the subject assigned the coloring tasks of FIGS. 13(A) to 13(C), respectively. Assume that the coloring tasks of FIGS. 13(A) to 13(C) are too easy, moderately difficult and too difficult for the subject, respectively.

The results of FIGS. 14(A) to 14(C) show the following facts. A too easy task causes the amount of input to be constantly high during the work, but hardly converts the negative feeling to the positive feeling since it can be done without concentration. A moderately difficult task causes the amount of input to be constantly high during the work, and converts the negative feeling to the positive feeling, which is maintained. A too difficult task causes the feeling and the amount of input during the work to vary, and causes the latter temporarily to decrease since the hand stops at difficult points in the task; the negative feeling occurs only before and after those points (times ta, tb in FIG. 14(C)) even if the positive feeling is generally maintained.

The assigning unit 240 thus repeatedly assigns tasks with different degrees of difficulty, according to the frequency of occurrence of the negative or positive feeling determined by the feeling determination unit 31 and the amount of input detected by the input detector 215 while the tasks are assigned. In other words, the assigning unit 240 decides an appropriate degree of difficulty for the user based on the patterns of occurrence of the positive and negative feelings stored in the feeling data memory 32 and the amount of input, and assigns a new task with that degree of difficulty, of the tasks stored in the task memory 241.

For example, if the amount of input is not less than a predetermined number and the negative feeling occurs more frequently than a predetermined frequency regardless of the amount of input, the assigning unit 240 determines that the task is too easy to produce an effect of changing feelings, and newly assigns a more difficult task. If the amount of input is not less than a predetermined number and the positive feeling occurs more frequently than a predetermined frequency regardless of the amount of input, the assigning unit 240 determines that the degree of difficulty of the task is appropriate and that an effect of changing feelings is produced, and assigns a new task with the same degree of difficulty as the former one. If the frequency of occurrence of the negative feeling is relatively high only when the amount of input decreases from above a predetermined number to below a predetermined number, the assigning unit 240 determines that the task is so difficult as to cause stress, and newly assigns an easier task.

The display 250 is an example of the output unit, shows the tasks assigned by the assigning unit 240, and shows the rate of occurrence of the positive feeling calculated by the effect evaluating unit 35 after the tasks are finished. The display 250 thereby makes the user realize the effect of changing feelings by use of the prevention device 3. The display 250 may regularly show which of the negative and positive feelings the result of determination by the feeling determination unit 31 is, while the task is assigned (during the work of the user), thereby notifying the user of the feeling during use. The timepiece 260 is the same as the timepiece 50 in the detection device 1.

FIG. 15 is a flowchart showing an operational example of the prevention device 3. First, the assigning unit 240 causes a task to be presented on the display 250 (S41). The image capturing unit 210 and feeling detector 220 then detect a pulse wave of the user, similarly to the detection device 1 (S42). The chaotic analyzer 25 calculates the maximum Lyapunov exponent $\lambda$ from the pulse wave detected in S42 (S43), while the feeling determination unit 31 compares that value with the threshold $\lambda t$ (S44).

The feeling determination unit 31 determines that the negative feeling occurs if $\lambda$ is not more than $\lambda t$ (Yes in S44), and that the positive feeling occurs if $\lambda$ is larger than $\lambda t$ (No in S44), and stores that result in the feeling data memory 32 (S45, 46). The input detector 215 detects the amount of input by the user using the input unit 200 (S47). Next, the assigning unit 240 decides the degree of difficulty of a task assigned to the user next time, based on the patterns of occurrence of the positive and negative feelings stored in S45, 46 and the amount of input detected in S47 (S48). The assigning unit 240 then determines whether the presentation of the tasks is finished (S49). If the presentation is not finished (No in S49), the process returns to S41. If finished (Yes in S49), the effect evaluating unit 35 calculates the rate of occurrence of the positive feeling (S50), causes that value to appear on the display 250 (S51), and terminates the process.

Since the prevention device 3 assigns tasks involving light work whose degree of difficulty is appropriate for the user, the user can concentrate on the tasks and consequently stops thinking about the negative feeling, which produces an effect of preventing senile dementia.

The detector of the detection device is not limited to one detecting pulse waves by image capturing, and may be a microwave Doppler sensor which can sense a heartbeat without touching the subject, or a sensor including electrodes or a photoelectric sensor worn all the time.

FIGS. 16(A) to 16(D) are diagrams showing detectors 10b, 10c. The detector 10b shown in FIGS. 16(A) to 16(C) includes a pair of electrodes 14L, 14R for sensing electrocardiograms. As shown in FIGS. 16(A) and 16(B), the electrodes 14L, 14R are provided on the left and right side surfaces of the housing of the detector 10b, respectively. The detector 10b senses an electrocardiogram of a subject, while the subject holds the housing thereof with both hands so that the left hand 70L and right hand 70R touch the electrodes 14L, 14R, respectively, as shown in FIG. 16(C). As described above, the detector detecting heartbeat information is not limited to one detecting pulse waves by image capturing, but may be a sensor including electrodes. Further, the electrode-type sensor, such as the detector 10b, may be provided with a band on the upper surfaces of the electrodes, for example, so that the subject can easily hold it for a long time.

The detector 10c shown in FIG. 16(D) is a watch-shaped pulse-wave sensor. The detector 10c includes a pulse-wave sensor 14 on the back surface of the watch, senses pulse waves while a user wears the band 16 of the watch on a hand 70, and shows a measured value on the display 15 of the watch. The watch-shaped sensor, such as the detector 10c, allows the subject to wear it without an uncomfortable feeling and to detect heartbeat information.

The invention claimed is:
1. A detection device comprising:
a detector detecting heartbeat information of a subject;
a generating unit generating a time-series data of pulse intervals based on the heartbeat information;
a calculating unit calculating a maximum Lyapunov exponent from the time-series data of pulse intervals;
a feeling determination unit determining whether the subject has a negative feeling with brain fatigue, anxiety or depression, or a positive feeling without brain fatigue, anxiety and depression, based on the maximum Lyapunov exponent;

a change determination unit determining whether the positive or negative feeling of the subject has changed, based on frequency of occurrence of the negative or positive feeling in a predetermined period; and an output unit outputting a result of determination by the change determination unit, wherein the predetermined period is three months or longer, and the change determination unit determines whether the subject suffers from mild cognitive impairment, based on the period and times of occurrence of the negative feeling as the frequency of occurrence.

2. The detection device according to claim 1, wherein the change determination unit determines whether the subject suffers from mild cognitive impairment, based on intra-day variations in the number of occurrences of the negative feeling.

3. The detection device according to claim 1, wherein the detector continuously captures images of a facial region of the subject automatically without any operations by the subject at least twice a day, morning and afternoon, during the predetermined period, and detects the heartbeat information based on variations in luminance of the captured images.

4. A detection device comprising:
a detector detecting heartbeat information of a subject;
a generating unit generating a time-series data of pulse intervals based on the heartbeat information;
a calculating unit calculating a maximum Lyapunov exponent from the time-series data of pulse intervals;
a feeling determination unit determining whether the subject has a negative feeling with brain fatigue, anxiety or depression, or a positive feeling without brain fatigue, anxiety and depression, based on the maximum Lyapunov exponent;
a change determination unit determining whether the positive or negative feeling of the subject has changed, based on frequency of occurrence of the negative or positive feeling in a predetermined period; and
an output unit outputting a result of determination by the change determination unit, wherein
the calculating unit calculates the maximum Lyapunov exponent ($\lambda$) by using the following Equation 1, and $$\lambda = \frac{1}{M}\sum_{k=1}^{M}\log_2 \frac{d(k)}{d(k-1)} \qquad \text{Equation 1}$$

M denotes the sum of sampling times of the time-series data of pulse intervals, d(k) denotes the time-series data of pulse intervals at time k, and d(k−1) denotes the time-series data of pulse intervals at time k−1.

5. The detection device according to claim 4, wherein the detector continuously captures images of a facial region of the subject automatically without any operations, and detects the heartbeat information based on variations in luminance of the captured images, and the feeling determination unit determines the feeling of the subject based on the maximum Lyapunov exponent calculated based on the heartbeat information detected from the continuously captured images if the amount of movement of the facial region in the images falls within a predetermined range.

6. The detection device according to claim 4, further comprising a feeling controller conducting guidance so that the subject concentrates and is lead to the positive feeling, wherein the predetermined period is a period during which the feeling controller continues the guidance, and the output unit is a display which shows a result of determination by the feeling determination unit during the guidance and a result of determination by the change determination unit after the guidance.

7. The detection device according to claim 6, wherein the feeling controller prompts the subject to draw a deep breath such that exhalation is slower than inhalation, thereby causing the subject to concentrate on breathing.

8. The detection device according to claim 7, wherein the feeling controller notifies the subject of timings of the inhalation and exhalation with a screen of the display.

9. The detection device according to claim 6, wherein the feeling controller plays music including a phrase longer than the period of breathing, thereby causing the subject to concentrate on the music.

10. The detection device according to claim 9, wherein the feeling controller controls the tempo of the music in accordance with the heart rate of the subject calculated from the heartbeat information.

11. The detection device according to claim 4, wherein the output unit is a display,
the detection device further comprises:
an input unit; and
an assigning unit assigning a task which requires input of the subject for processing an object shown on the display, wherein
the predetermined period is a period during which the assigning unit assigns the task, and
the display shows the task and shows a result of determination by the change determination unit after the task is finished.

12. The detection device according to claim 11, further comprising:
a memory storing tasks assigned by the assigning unit, the tasks varying in degree of difficulty; and
an input detector detecting the amount of input for processing the object, wherein
the assigning unit repeatedly assigns tasks with different degrees of difficulty, according to the frequency of occurrence of the negative or positive feeling and the amount of input in the predetermined period.

13. The detection device according to claim 11, wherein the assigning unit assigns, as the task, one which requires coloring in regions divided by lines shown on the display.

14. The detection device according to claim 11, wherein the assigning unit assigns, as the task, one which requires copying letters shown on the display onto the display by hand.

15. The detection device according to claim 6, wherein the display shows to what extent the negative feeling has changed to the positive feeling, based on frequency of occurrence of the positive feeling in the predetermined period, as the result of determination by the change determination unit.

16. The detection device according to claim 4, wherein the feeling determination unit determines that the subject has the negative feeling if the maximum Lyapunov exponent ($\lambda$) is less than −0.6.

17. A detection device comprising:
a detector detecting heartbeat information of a subject;
a generating unit generating a time-series data of pulse intervals based on the heartbeat information;
a calculating unit calculating a maximum Lyapunov exponent from the time-series data of pulse intervals;

a feeling determination unit determining whether the subject has a negative feeling with brain fatigue, anxiety or depression, or a positive feeling without brain fatigue, anxiety and depression, based on the maximum Lyapunov exponent; and a feeling controller conducting guidance so that the subject concentrates and is lead to the positive feeling, wherein determination by the feeling determination unit is implemented during feeling control, the calculating unit calculates the maximum Lyapunov exponent (λ) by using the following Equation 1, and $$\lambda = \frac{1}{M}\sum_{k=1}^{M}\log_2 \frac{d(k)}{d(k-1)} \quad \text{Equation 1}$$

M denotes the sum of sampling times of the time-series data of pulse intervals, d(k) denotes the time-series data of pulse intervals at time k, and d(k−1) denotes the time-series data of pulse intervals at time k−1.

18. The detection device according to claim 17, wherein the detector detecting heartbeat information of the subject is a means for detecting from a face image without touching.

19. The detection device according to claim 17, wherein a rate of the positive feeling is calculated and displayed as degree of achievement.

20. A detection device comprising:
a detector detecting heartbeat information of a subject;
a generating unit generating a time-series data of pulse intervals based on the heartbeat information;
a calculating unit calculating a maximum Lyapunov exponent from the time-series data of pulse intervals;
a feeling determination unit determining whether the subject has a negative feeling with brain fatigue, anxiety or depression, or a positive feeling without brain fatigue, anxiety and depression, based on the time-series data of pulse intervals;
a feeling controller conducting guidance so that the subject concentrates and is lead to the positive feeling;
a change determination unit determining whether the positive or negative feeling of the subject has changed, based on frequency of occurrence of the negative or positive feeling in a period during which the feeling controller continues the guidance; and
an output unit outputting a result of determination by the change determination unit, wherein the calculating unit calculates the maximum Lyapunov exponent (λ) by using the following Equation 1, and $$\lambda = \frac{1}{M}\sum_{k=1}^{M}\log_2 \frac{d(k)}{d(k-1)} \quad \text{Equation 1}$$

M denotes the sum of sampling times of the time-series data of pulse intervals, d(k) denotes the time-series data of pulse intervals at time k, and d(k−1) denotes the time-series data of pulse intervals at time k−1.

21. A detection device comprising:
a detector detecting heartbeat information of a subject;
a generating unit generating a time-series data of pulse intervals based on the heartbeat information;
a calculating unit calculating a maximum Lyapunov exponent from the time-series data of pulse intervals;
a feeling determination unit determining whether the subject has a negative feeling with brain fatigue, anxiety or depression, or a positive feeling without brain fatigue, anxiety and depression, based on the time-series data of pulse intervals;
a display;
an input unit;
an assigning unit assigning a task which requires input of the subject for processing an object shown on the display; and
a change determination unit determining whether the positive or negative feeling of the subject has changed, based on frequency of occurrence of the negative or positive feeling in a period during which the assigning unit assigns the task,
wherein the display shows the task and shows a result of determination by the change determination unit after the task is finished
the calculating unit calculates the maximum Lyapunov exponent (λ) by using the following Equation 1, and $$\lambda = \frac{1}{M}\sum_{k=1}^{M}\log_2 \frac{d(k)}{d(k-1)} \quad \text{Equation 1}$$

M denotes the sum of sampling times of the time-series data of pulse intervals, d(k) denotes+ the time-series data of pulse intervals at time k, and d(k−1) denotes the time-series data of pulse intervals at time k−1.

* * * * *